United States Patent
Hee-Hanson et al.

(10) Patent No.: US 12,420,017 B1
(45) Date of Patent: Sep. 23, 2025

(54) DAMPING DEVICE FOR A MEDICAMENT DELIVERY DEVICE

(71) Applicant: Genzyme Corporation, Cambridge, MA (US)

(72) Inventors: Alexander Hee-Hanson, Melbourn (GB); Thomas Lever, Melbourn (GB); Michael Parrott, Melbourn (GB); Robert Wilson, Melbourn (GB); Haiming Wu, Cambridge, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 19/063,656

(22) Filed: Feb. 26, 2025

(51) Int. Cl.
| | |
|---|---|
| *A61M 5/20* | (2006.01) |
| *A61M 5/32* | (2006.01) |
| *A61M 5/31* | (2006.01) |

(52) U.S. Cl.
CPC ........ *A61M 5/2033* (2013.01); *A61M 5/3202* (2013.01); *A61M 5/3243* (2013.01); *A61M 2005/2073* (2013.01); *A61M 2005/3143* (2013.01)

(58) Field of Classification Search
CPC .............. A61M 5/2033; A61M 5/3202; A61M 5/3243; A61M 2005/2073; A61M 2005/3143
See application file for complete search history.

(56) References Cited

U.S. PATENT DOCUMENTS

| | | |
|---|---|---|
| 2,522,961 A | 9/1950 | William |
| 2,633,267 A | 3/1953 | Lebus |
| 3,886,513 A | 5/1975 | Smith et al. |
| 4,801,295 A | 1/1989 | Spencer |
| 5,045,062 A | 9/1991 | Henson |
| 5,176,275 A | 1/1993 | Bowie |
| 5,328,484 A | 7/1994 | Somers et al. |
| 5,396,051 A | 3/1995 | Kuhn et al. |
| 5,478,316 A | 12/1995 | Bitdinger et al. |
| 5,505,324 A | 4/1996 | Danico |
| 5,505,706 A | 4/1996 | Maus et al. |

(Continued)

FOREIGN PATENT DOCUMENTS

| | | |
|---|---|---|
| DE | 3921747 A1 | 1/1991 |
| EP | 3501577 A1 | 6/2019 |

(Continued)

OTHER PUBLICATIONS

Hamers-Casterman et al., "Naturally occurring antibodies devoid of light chains," Nature, Jun. 3, 1993, 363(6428):446-448.

(Continued)

*Primary Examiner* — Tasnim Mehjabin Ahmed
(74) *Attorney, Agent, or Firm* — Fish & Richardson P.C.

(57) ABSTRACT

A damping device for a medicament delivery device, comprising: a generally cylindrical first collar; a housing comprising a generally annular cavity configured to receive at least a portion of the first collar; wherein the first collar is configured to be rotatable relative to the housing about a central longitudinal axis of the damping device, and wherein the cavity is configured to contain a fluid for impeding rotational movement of the first collar relative to the housing; and a sealing arrangement configured to fluidly seal an interface between the housing and the first collar.

20 Claims, 10 Drawing Sheets

(56) References Cited

U.S. PATENT DOCUMENTS

| | | |
|---|---|---|
| 5,536,917 A | 7/1996 | Suppelsa et al. |
| 5,622,274 A | 4/1997 | Bright |
| 5,738,658 A | 4/1998 | Maus et al. |
| 5,984,899 A | 11/1999 | D'Alessio et al. |
| 6,080,461 A | 6/2000 | Wozniak et al. |
| 6,394,985 B1 | 5/2002 | Lin |
| 7,762,981 B2 | 7/2010 | Dacquay et al. |
| 7,887,506 B1 | 2/2011 | Smolyarov et al. |
| 7,918,824 B2 | 4/2011 | Bishop et al. |
| 8,133,198 B2 | 3/2012 | Neer |
| 8,409,138 B2 | 4/2013 | James et al. |
| 8,734,394 B2 | 5/2014 | Adams et al. |
| 9,044,553 B2 | 6/2015 | James et al. |
| 9,402,957 B2 | 8/2016 | Adams et al. |
| 9,474,780 B2 | 10/2016 | Bokvist et al. |
| 9,872,961 B2 | 1/2018 | Fourt et al. |
| 10,118,001 B2 | 11/2018 | Fourt et al. |
| 10,314,981 B2 | 6/2019 | Sampson et al. |
| 10,350,362 B2 | 7/2019 | Dennis, Jr. et al. |
| 10,363,377 B2 | 7/2019 | Atterbury et al. |
| 11,298,462 B2 | 4/2022 | Atterbury et al. |
| 11,331,432 B2 | 5/2022 | Holmqvist et al. |
| 11,357,820 B2 | 6/2022 | Corvari et al. |
| 11,369,751 B2 | 6/2022 | Ruan et al. |
| 11,452,821 B2 | 9/2022 | LaFever et al. |
| 2002/0055712 A1 | 5/2002 | Neracher |
| 2004/0039336 A1 | 2/2004 | Amark et al. |
| 2005/0101919 A1 | 5/2005 | Brunnberg |
| 2005/0273061 A1 | 12/2005 | Hommann et al. |
| 2006/0224124 A1 | 10/2006 | Scherer |
| 2007/0270777 A1 | 11/2007 | Dacquay et al. |
| 2008/0097311 A1 | 4/2008 | Dacquay et al. |
| 2008/0097390 A1 | 4/2008 | Dacquay et al. |
| 2008/0269692 A1 | 10/2008 | James et al. |
| 2009/0036868 A1 | 2/2009 | Pinedjian et al. |
| 2009/0281496 A1 | 11/2009 | Matusch |
| 2010/0049125 A1* | 2/2010 | James ............... A61M 5/2033 604/110 |
| 2010/0211005 A1 | 8/2010 | Edwards et al. |
| 2011/0054414 A1 | 3/2011 | Shang et al. |
| 2011/0144594 A1 | 6/2011 | Sund et al. |
| 2011/0202011 A1 | 8/2011 | Wozencroft |
| 2011/0319813 A1 | 12/2011 | Kamen et al. |
| 2013/0237921 A1 | 9/2013 | Lannan et al. |
| 2013/0267897 A1 | 10/2013 | Kemp et al. |
| 2014/0236076 A1 | 8/2014 | Marshall et al. |
| 2014/0249483 A1 | 9/2014 | Kiilerich et al. |
| 2014/0263156 A1 | 9/2014 | Newsom et al. |
| 2014/0276637 A1 | 9/2014 | Massey, Jr. |
| 2015/0246180 A1 | 9/2015 | Fenlon et al. |
| 2015/0273162 A1 | 10/2015 | Holmqvist |
| 2016/0001015 A1 | 1/2016 | Kucuk et al. |
| 2016/0354555 A1 | 12/2016 | Gibson et al. |
| 2016/0367763 A1 | 12/2016 | Tschirren et al. |
| 2017/0182253 A1* | 6/2017 | Folk .................... F16F 9/16 |
| 2017/0215699 A1 | 8/2017 | Ouyang et al. |
| 2017/0216526 A1 | 8/2017 | Brereton et al. |
| 2017/0224929 A1 | 8/2017 | Sampson et al. |
| 2017/0246403 A1 | 8/2017 | Cowe et al. |
| 2017/0361034 A1 | 12/2017 | Scheller et al. |
| 2017/0368259 A1* | 12/2017 | Olson ............... A61M 5/5086 |
| 2018/0250471 A1 | 9/2018 | Grimoldby et al. |
| 2018/0339114 A1 | 11/2018 | Wendland et al. |
| 2019/0030249 A1 | 1/2019 | Gonzalez et al. |
| 2019/0192785 A1 | 6/2019 | Wendland et al. |
| 2019/0366000 A1 | 12/2019 | Cowe et al. |
| 2020/0114041 A1 | 4/2020 | Alas et al. |
| 2020/0206429 A1* | 7/2020 | Hering ............ A61M 5/31511 |
| 2020/0316314 A1 | 10/2020 | Buri et al. |
| 2021/0077732 A1 | 3/2021 | Egelhofer |
| 2021/0196900 A1 | 7/2021 | Apply et al. |
| 2022/0015429 A1 | 1/2022 | Brown et al. |
| 2022/0176042 A1 | 6/2022 | Belisle |
| 2022/0395640 A1 | 12/2022 | Schwartzentruber |
| 2023/0001099 A1 | 1/2023 | Dunn |
| 2023/0238105 A1 | 7/2023 | Schneider et al. |
| 2023/0347074 A1 | 11/2023 | Gavin |
| 2024/0009397 A1 | 1/2024 | In et al. |
| 2024/0189513 A1* | 6/2024 | Payne ............... A61M 5/2033 |

FOREIGN PATENT DOCUMENTS

| | | |
|---|---|---|
| WO | WO 2002/047746 A1 | 6/2002 |
| WO | WO 2004/058820 A2 | 7/2004 |
| WO | WO 2004/068820 A2 | 8/2004 |
| WO | WO 2005/018629 A1 | 3/2005 |
| WO | WO 2006/003388 A2 | 1/2006 |
| WO | WO 2006/030220 A1 | 3/2006 |
| WO | WO 2011/109205 A2 | 9/2011 |
| WO | WO 2016/081238 A1 | 5/2016 |
| WO | WO 2019/074788 A1 | 4/2019 |
| WO | WO 2020/190529 A1 | 9/2020 |

OTHER PUBLICATIONS

Holt et al., "Domain antibodies: proteins for therapy," Trends in Biotechnology, Nov. 2003, 21(11):484-490.

Muyldermans, "Single domain camel antibodies: current status," Reviews in Molecular Biotechnology, Jun. 2001, 74(4):277-302.

Needle-based injection systems for medical use requirements and test methods, Part 1: Needle injection systems, ISO 11608-1:2014(E), Third Edition, Switzerland, ISO, Dec. 15, 2014, pp. 1-13.

Ward et al., "Binding activities of a repertoire of single immunoglobulin variable domains secreted from *Escherichia coli*," Nature, Oct. 1, 1989, 341(6242):544-546.

* cited by examiner

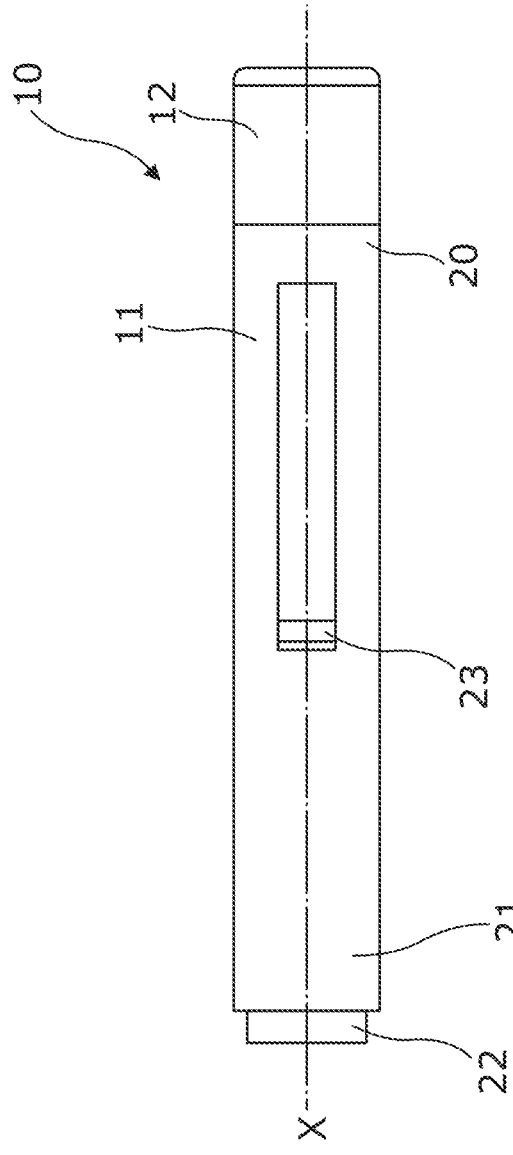
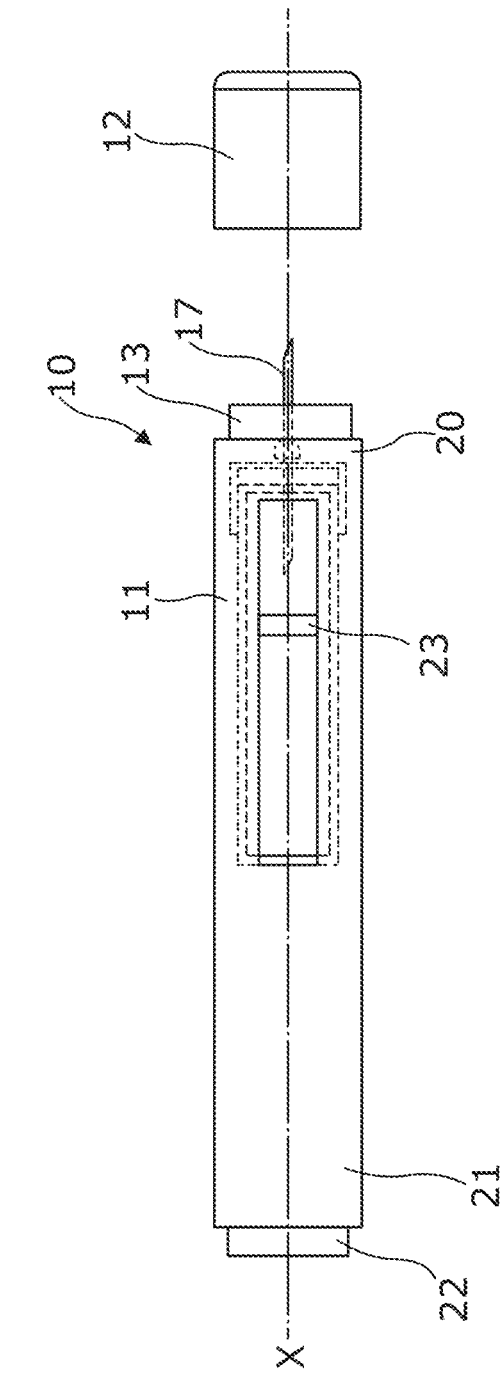
FIG. 1A
FIG. 1B

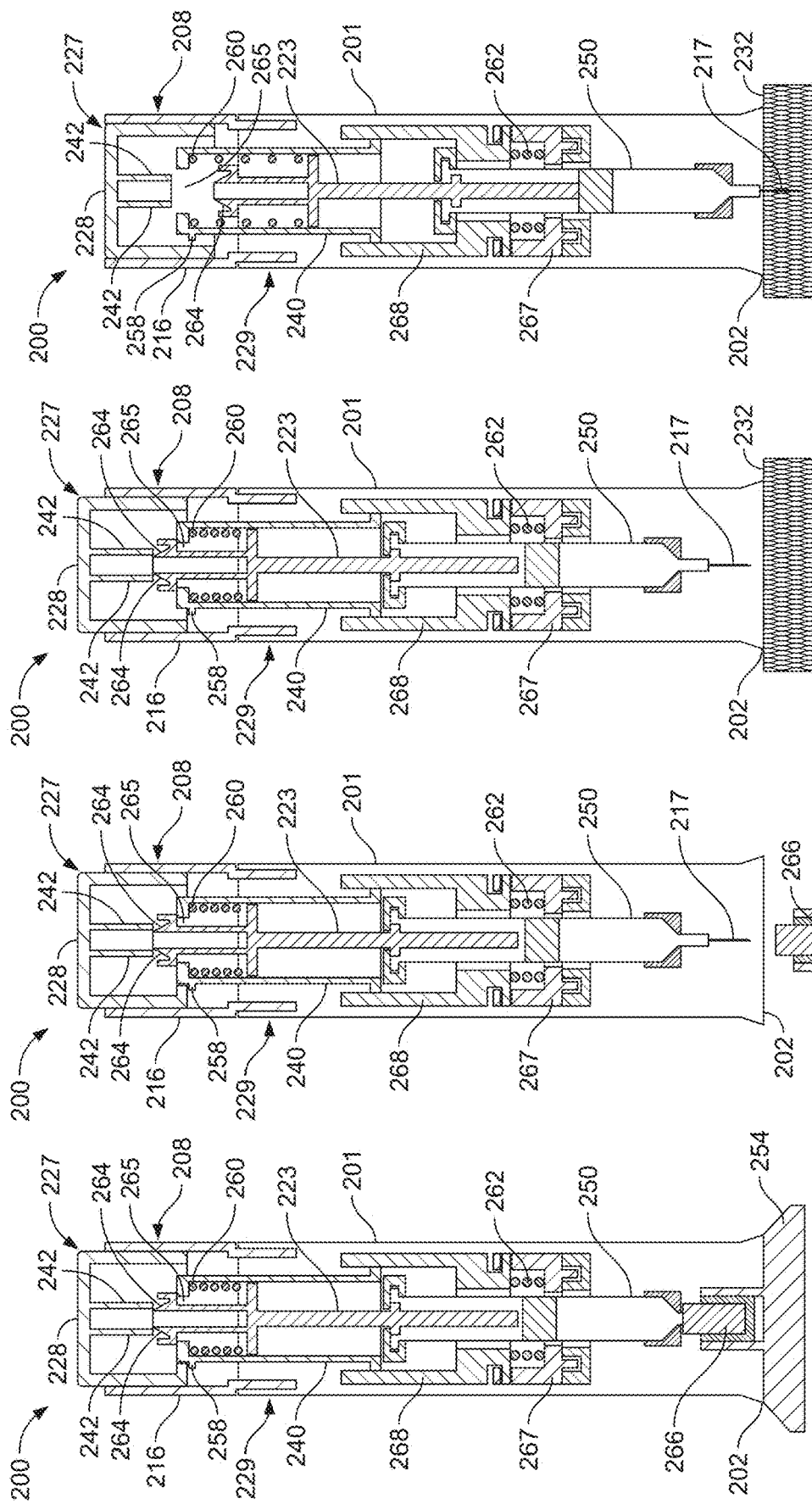

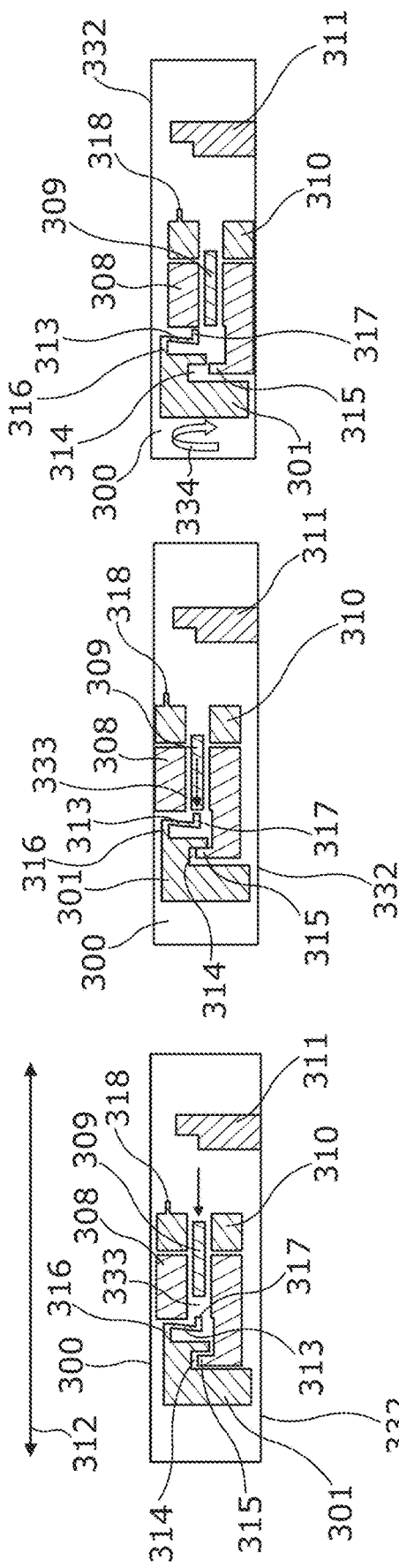
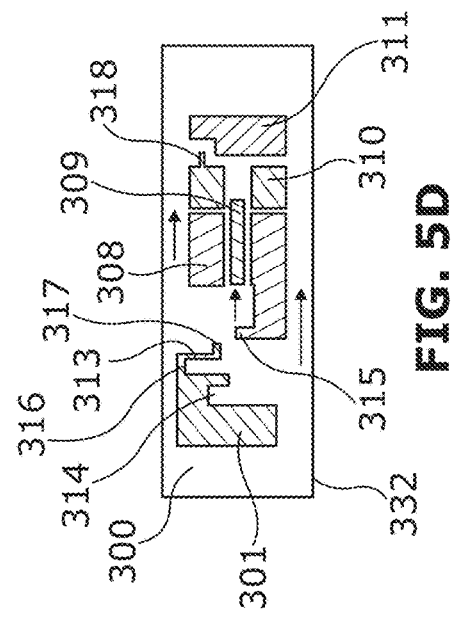

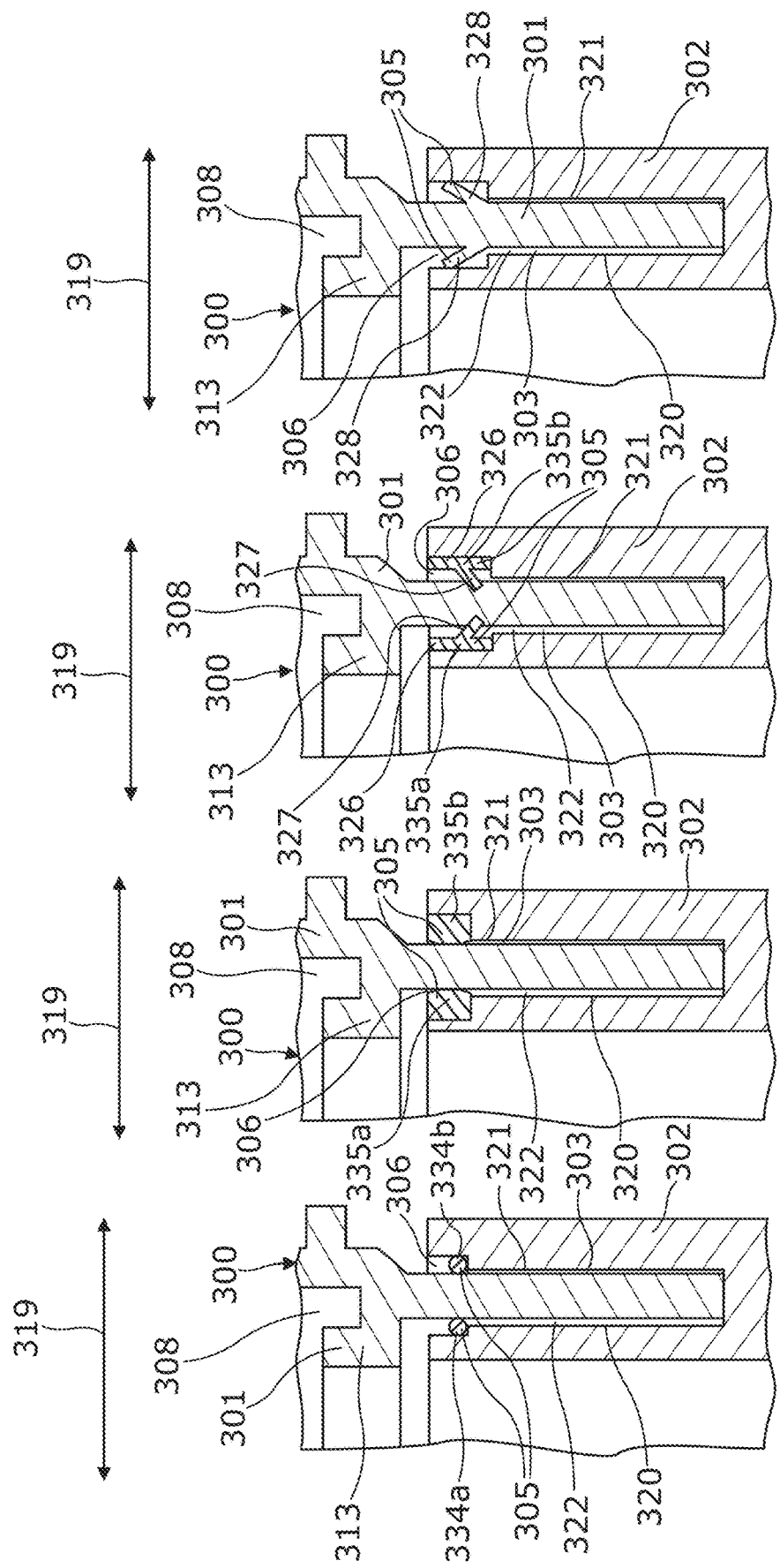

DAMPING DEVICE FOR A MEDICAMENT DELIVERY DEVICE

TECHNICAL FIELD

The present disclosure relates to a damping device for a medicament delivery device, and to a medicament delivery device comprising a damping device.

BACKGROUND

Medicament delivery devices, such as auto-injectors, are known in the art for dispensing medicament to an injection site of a patient. There may sometimes be a need within a medicament delivery device to create a time delay between the change of state of one part and the triggering of another mechanism. For example, it may be desired to provide a time delay between a plunger reaching a certain position and the triggering of a needle retraction mechanism and/or the provision of end of dose feedback. After all of the medicament has been delivered from a medicament delivery device, it may be desirable that the needle should be retracted and that the user should be given feedback that the medicament has been delivered. It may be desirable that the needle should not be retracted and end of dose feedback should not be given before the end of the dose has been reached. Instantaneously triggering needle retraction at the exact point that end of dose is reached may risk needle retraction not being triggered as a worst-case scenario. Furthermore, if the needle is retracted as soon as the plunger reaches the end of dose, there may be a risk that not all of the medicament has been delivered to the patient through the needle. Providing a time delay may reduce or avoid the risk that the needle is retracted and/or end of dose feedback is given before all the medicament has been delivered.

SUMMARY

A first aspect of this disclosure provides a damping device for a medicament delivery device, comprising: a generally cylindrical first collar; a housing comprising a generally annular cavity configured to receive at least a portion of the first collar; wherein the first collar is configured to be rotatable relative to the housing about a central longitudinal axis of the damping device, and wherein the cavity is configured to contain a fluid for impeding rotational movement of the first collar relative to the housing; and a sealing arrangement configured to fluidly seal an interface between the housing and the first collar.

In some embodiments, at least a portion of the first collar is received in the cavity, and the cavity also contains fluid for impeding rotational movement of the first collar relative to the housing.

In some embodiments, the housing is generally cylindrical.

In some embodiments, the first collar is generally hollow.

In some embodiments, the housing and the first collar are configured to be arranged concentrically with one another about the central longitudinal axis.

In some embodiments, the first collar is configured to be slidably received in the housing.

In some embodiments, the housing is configured to receive a first portion of the first collar.

In some embodiments, the first collar is biased to rotate relative to the housing by a biasing means.

In some embodiments, the biasing means comprises a spring.

In some embodiments, the generally annular cavity comprises an inner surface and an outer surface.

In some embodiments, the generally annular cavity comprises a generally annular cross-sectional profile in a plane that is generally normal to the central longitudinal axis.

In some embodiments, the generally annular cross-sectional profile comprises an inner radius and an outer radius.

In some embodiments, the inner radius defines an inner surface of the generally annular cavity, and the outer radius defines an outer surface of the generally annular cavity.

In some embodiments, the cavity comprises a cavity thickness which is equal to the difference between the outer radius and the inner radius.

In some embodiments, in the portion of the first collar which is configured to be received in the cavity, the first collar comprises a first wall thickness.

In some embodiments, the cavity thickness is configured to be greater than the first wall thickness.

In some embodiments, when said at least a portion of the first collar is received in the generally annular cavity of the housing, there is a gap between the first collar and the inner and/or outer surfaces of the cavity.

In some embodiments, when said at least a portion of the first collar is received in the generally annular cavity of the housing, there is a spacing in the cavity.

In some embodiments, the gap or spacing in the cavity is configured to be filled with the fluid.

In some embodiments, the gap or spacing in the cavity is configured to contain fluid, for example grease, for slowing down the rotation of the first collar in the cavity, thus damping the first collar's rotation.

In some embodiments, the cavity comprises an open end into which the first collar is configured to be inserted.

In some embodiments, the cavity is configured to receive the first collar such that a first portion of the first collar is arranged within the cavity, to be circumferentially concentrically received in and circumscribed by the housing, and a second portion of the first collar is arranged to protrude from the housing.

In some embodiments, the first collar is configured to be rotatable within the cavity about the central longitudinal axis relative to the housing.

In some embodiments, the sealing arrangement comprises an elastomeric material, such as silicone, viton, ethylene propylene diene monomer, or nitrile rubber for example, and/or a thermoplastic material, such as polyethylene, polypropylene, acrylonitrile butadiene styrene, or polycarbonate for example.

In some embodiments, the first collar comprises the sealing arrangement.

In some embodiments, the housing comprises the sealing arrangement.

In some embodiments, the sealing arrangement is coupled to, overmolded with, or integrally formed with, the first collar.

In some embodiments, the sealing arrangement is coupled to, overmolded with, or integrally formed with, the housing.

In some embodiments, the sealing arrangement is configured to axially seal the interface between the housing and the first collar along an axial direction that is generally parallel to the central longitudinal axis, and/or to radially seal the interface between the housing and the first collar along a radial direction that is generally normal to the central longitudinal axis.

In some embodiments, the sealing arrangement is configured to fluidly seal an open end of the cavity, at an inner interface between an inner surface of the first collar and an inner surface of the cavity and/or at an outer interface between an outer surface of the first collar and an outer surface of the cavity.

In some embodiments, the sealing arrangement comprises an axial seal arranged to fluidly seal the interface between the housing and the first collar along an axial direction that is generally parallel to the central longitudinal axis of the damping device.

In some embodiments, along the central longitudinal axis, the sealing arrangement is arranged between the housing and the first collar.

In some embodiments, the axial seal comprises one or more O-rings.

In some embodiments, the axial seal comprises a first O-ring and a second O-ring.

In some embodiments, the second O-ring has a larger outer diameter than the first O-ring.

In some embodiments, the first O-ring is arranged proximate to an inner surface of the cavity, and the second O-ring is arranged proximate to an outer surface of the cavity.

In some embodiments, the first and second O-rings are each arranged axially between the housing and the first collar along the central longitudinal axis.

In some embodiments, the axial seal comprises a first O-ring arranged proximate to an inner surface of the cavity, and/or a second O-ring arranged proximate to an outer surface of the cavity.

In some embodiments, each of the one or more O-rings comprises a generally circular, quadrilateral or triangular cross-sectional profile.

In some embodiments, each of the one or more O-rings is formed from an elastomeric material, such as silicone, viton, ethylene propylene diene monomer, or nitrile rubber for example.

In some embodiments, the axial seal comprises at least one first axial sealing element coupled to or integrally formed with the housing, and/or at least one second axial sealing element coupled to or integrally formed with the first collar.

In some embodiments, the axial seal comprises at least two first axial sealing elements coupled to, overmolded with, or integrally formed with the housing.

In some embodiments, the at least two first axial sealing elements comprise a first axial seal arranged proximate to an inner surface of the cavity, and a second axial seal arranged proximate to an outer surface of the cavity.

In some embodiments, the first and second axial seals are generally annular.

In some embodiments, each of the at least one first or second axial sealing elements comprises a generally triangular or a generally arrow shaped cross-sectional profile.

In some embodiments, each of the at least one first axial sealing elements is overmolded with the housing, and/or each of the at least one second axial sealing elements is overmolded with the first collar.

In some embodiments, each of the at least one first and/or second axial sealing elements comprises an elastomeric material, such as silicone, viton, ethylene propylene diene monomer, or nitrile rubber for example.

In some embodiments, the axial seal comprises two first axial sealing elements overmolded with or coupled to the housing.

In some embodiments, the housing comprises a first generally annular recess and a second generally annular recess, each for receiving a respective one of the two first axial sealing elements.

In some embodiments, each of the first and second axial seals comprises a coupling portion which is arranged to protrude into and be received in a respective one of the first and second generally annular recesses.

In some embodiments, each of the first and second generally annular recesses has a generally rectangular cross-sectional profile.

In some embodiments, each of the first and second axial seals further comprises a sealing portion integrally formed with the coupling portion and configured to protrude therefrom and out away from the respective recess in the housing.

In some embodiments, each of the sealing portions comprises a generally triangular cross-sectional profile.

In some embodiments, the sealing arrangement comprises a radial seal arranged to fluidly seal the interface between the housing and the first collar along a radial direction that is generally normal to the central longitudinal axis of the damping device.

In some embodiments, the sealing arrangement comprises an axial seal arranged to fluidly seal the interface between the housing and the first collar along an axial direction that is generally parallel to the central longitudinal axis of the damping device, and a radial seal arranged to fluidly seal the interface between the housing and the first collar along a radial direction that is generally normal to the central longitudinal axis of the damping device.

In some embodiments, the radial seal is arranged proximate to an inner surface of the cavity, and the axial seal is arranged proximate to an outer surface of the cavity.

In some embodiments, the radial seal is arranged proximate to an outer surface of the cavity, and the radial seal is arranged proximate to an inner surface of the cavity.

In some embodiments, a radial and/or axial seal is arranged proximate to an outer surface of the cavity, and/or a radial and/or axial seal is arranged proximate to an inner surface of the cavity.

In some embodiments, along the radial direction, the sealing arrangement is arranged between the housing and the first collar.

In some embodiments, the radial seal comprises one or more O-rings.

In some embodiments, the radial seal comprises a first O-ring and a second O-ring.

In some embodiments, the second O-ring has a larger outer diameter than the first O-ring.

In some embodiments, the first O-ring is arranged proximate to an inner surface of the cavity, and the second O-ring is arranged proximate to an outer surface of the cavity.

In some embodiments, the first and second O-rings are each arranged radially between the housing and the first collar along the radial direction.

In some embodiments, the radial seal comprises a first O-ring arranged proximate to an inner surface of the cavity, and/or a second O-ring arranged proximate to an outer surface of the cavity.

In some embodiments, each of the one or more O-rings comprises a generally circular, quadrilateral or triangular cross-sectional profile.

In some embodiments, each of the one or more O-rings is formed from an elastomeric material, such as silicone, viton, ethylene propylene diene monomer, or nitrile rubber for example.

In some embodiments, the radial seal comprises at least one first radial sealing element coupled to or integrally formed with the housing, and/or at least one second radial sealing element coupled to or integrally formed with the first collar.

In some embodiments, the radial seal comprises at least one seal comprising a generally rectangular cross-sectional profile.

In some embodiments, the radial seal comprises at least one seal which is inclined relative to the central longitudinal axis.

In some embodiments, the radial seal comprises at least one first radial sealing element coupled to, overmolded with, or integrally formed with the housing.

In some embodiments, the at least one first radial sealing element comprises a first radial seal and a second radial seal.

In some embodiments, the first radial seal is arranged proximate to an inner surface of the cavity, and the second radial seal is arranged proximate to an outer surface of the cavity.

In some embodiments, the first radial seal and the second radial seal are overmolded onto the housing.

In some embodiments, the first and second radial seals comprise an elastomeric material, for example silicone, viton, ethylene propylene diene monomer, or nitrile rubber.

In some embodiments, the first and second radial seals are each configured to protrude inwards into the cavity.

In some embodiments, the first and second radial seals are configured generally to be a mirror image of one another.

In some embodiments, each of the first and second radial seals is generally annular.

In some embodiments, each of the first and second radial seals has a generally quadrilateral cross-sectional profile, for example a generally square or rectangular cross-sectional profile.

In some embodiments, each of the first and second radial seals comprises a generally convex edge or face arranged to be generally parallel to the central longitudinal axis.

In some embodiments, each of the generally convex edges or faces is arranged to protrude along the radial direction towards and into the cavity.

In some embodiments, each of the generally convex edges or faces is configured to interface with, for example to contact and/or abut with, the first collar, when the first collar is received in the cavity.

In some embodiments, each of the first and second radial seals is configured to interface with, for example to contact and/or abut with, the first collar, when the first collar is received in the cavity.

In some embodiments, the first radial seal is arranged to protrude from an inner surface of the cavity radially outwards along the radial direction, and the second seal is arranged to protrude from an outer surface of the cavity radially inwards along the radial direction.

In some embodiments, the cross-sectional profiles of the first and second radial seals are configured to be generally a mirror image of one another.

In some embodiments, at least a portion of each of the one or more first and/or second radial sealing elements is configured to be angled relative to the central longitudinal axis.

In some embodiments, each of the one or more first and/or second radial sealing elements is generally inclined relative to the central longitudinal axis.

In some embodiments, each of the one or more first and/or second radial sealing elements comprises a coupling portion and an inclined sealing portion integrally formed with the coupling portion.

In some embodiments, the coupling portion has a generally rectangular cross-sectional profile and is oriented to be generally parallel to the longitudinal direction, and the inclined sealing portion is configured to protrude from the coupling portion into and towards the cavity.

In some embodiments, the inclined sealing portion is arranged to be angled relative to the longitudinal axis.

In some embodiments, the radial seal comprises at least one first radial sealing element coupled to, overmolded with or integrally formed with the housing, wherein the at least one first radial sealing element comprises a first radial seal arranged proximate to an inner surface of the cavity and a second radial seal arranged proximate to an outer surface of the cavity.

In some embodiments, the first and second radial seals each comprise a coupling portion and an inclined sealing portion integrally formed with the coupling portion and arranged to protrude from the coupling portion, wherein the inclined sealing portion or angled relative to the longitudinal axis.

In some embodiments, the inclined sealing portions of the first and second radial seals are arranged to be a mirror image of one another, for example to form a V-shape.

In some embodiments, the inclined sealing portion of the first radial seal is arranged to protrude radially outwards along the radial direction into the cavity in a longitudinal direction from a proximal end of the device to a distal end of the device.

In some embodiments, the inclined sealing portion of the second radial seal is arranged to protrude radially inwards along the radial direction into the cavity in a longitudinal direction from a proximal end of the device to a distal end of the device.

In some embodiments, the radial seal comprises at least one second radial sealing element coupled to, overmolded with, or integrally formed with the first collar.

In some embodiments, the at least one second radial sealing element is coupled to, overmolded with, or integrally formed with a first portion of the first collar which is configured to be received in the cavity.

In some embodiments, the at least one second radial sealing element comprises a first radial seal and a second radial seal.

In some embodiments, the first radial seal is arranged proximate to an inner surface of the cavity, and the second radial seal is arranged proximate to an outer surface of the cavity.

In some embodiments, the at least one second radial sealing element is formed from a thermoplastic material, for example polyethylene, polypropylene, acrylonitrile butadiene styrene, or polycarbonate.

In some embodiments, the first radial seal is arranged to protrude radially inwards from an inner surface of the first collar towards an inner surface of the cavity, and the second radial seal is arranged to protrude radially outwards from an outer surface of the first collar towards an outer surface of the cavity.

In some embodiments, the first and second radial seals are configured to generally be a mirror image of one another, and to form a V-shape.

In some embodiments, the first and second radial seals of the at least one second radial sealing element may have any one or more of the features described above in relation to the first and second radial seals of the at least one first radial sealing element.

In some embodiments, each of the at least one first and second radial sealing elements comprises an inclined portion that is angled relative to the central longitudinal axis of the damping device.

In some embodiments, the sealing arrangement is overmolded onto the housing and/or onto the first collar.

In some embodiments, the housing and/or the first collar are shaped such that the interface between the housing and the first collar defines a fluid flow path comprising one or more bends, and the sealing arrangement comprises said fluid flow path, which is generally tortuous or defines a labyrinth seal between the housing and the first collar, to impede the leakage of fluid out from the cavity.

In some embodiments, the sealing arrangement comprises a labyrinth seal.

In some embodiments, the housing and the first collar are configured such that at the interface where they are adjacent to one another and/or abut one another, the fluid flow path defined therebetween comprises one or more bends.

In some embodiments, the first collar comprises one or more first protruding portions, and the housing comprises one or more second protruding portions.

In some embodiments, at least a portion of the fluid flow path is defined between the one or more first protruding portions and the one or more second protruding portions.

In some embodiments, the one or more first protruding portions of the first collar are configured to extend in a longitudinal direction that is generally parallel to the central longitudinal axis, towards the housing.

In some embodiments, the one or more second protruding portions of the housing are configured to extend in a longitudinal direction that is generally parallel to the central longitudinal axis, towards the first collar.

In some embodiments, at least one of the one or more first protruding portions is configured to fit together with at least one of the one or more second protruding portions.

In some embodiments, the first collar comprises two first protruding portions, and the housing comprises two second protruding portions.

In some embodiments, a first one of the first protruding portions and a first one of the second protruding portions are arranged proximate to an inner surface of the cavity, and a second one of the first protruding portions and a second one of the second protruding portions are arranged proximate to an outer surface of the cavity.

In some embodiments, each of the one or more first protruding portions is integrally formed with the first collar.

In some embodiments, each of the one or more second protruding portions is integrally formed with the housing.

In some embodiments, each of the one or more first protruding portions and each of the one or more second protruding portions has a generally rectangular cross-sectional profile and is oriented to be generally parallel to the central longitudinal axis.

In some embodiments, each of the one or more first protruding portions and each of the one or more second protruding portions is configured to be generally annular.

In some embodiments, each of the one or more first and second protruding portions is formed from a thermoplastic material, for example polyethylene, polypropylene, acrylonitrile butadiene styrene, or polycarbonate.

In some embodiments, the fluid comprises grease.

In some embodiments, the fluid comprises a viscous fluid.

In some embodiments, the damping device further comprises a generally cylindrical second collar configured to circumscribe at least a portion of the first collar, wherein the first and second collars are arrangeable in a first state in which they are rotationally and axially fixed relative to one another, and a second state in which they are rotationally and axially moveable relative to one another.

In some embodiments, at least a portion of the second collar is generally hollow.

In some embodiments, the housing is configured to receive a first portion of the first collar and the second collar is configured to receive a second portion of the first collar.

In some embodiments, the first collar is configured to be rotationally movable relative to the housing and relative to the second collar about the central longitudinal axis.

In some embodiments, the first collar comprises a first coupling element configured to be received by the second collar to couple the first and second collars to one another in the first state, wherein the first coupling element is deformable or deflectable such that deforming or deflecting the first coupling element causes the first and second collars to be decouplable from one another, to permit the first collar to rotate relative to the second collar and/or to permit the second collar to axially move relative to the first collar.

In some embodiments, the first coupling element is configured to rotationally couple the first collar to the second collar, such that the first and second collars may not be rotated relative to one another when the first coupling element is received by the second collar.

In some embodiments, the first collar comprises a receiving element configured to receive a second coupling element of the second collar, wherein deforming or deflecting the first coupling element causes the first collar to rotate relative to the second collar, which causes the second coupling element to move out from the receiving element, which permits the second collar to move axially relative to the first collar.

In some embodiments, the second coupling element is configured to axially couple the first collar to the second collar, such that the first and second collars may not be moved axially relative to one another along the central longitudinal axis when the second coupling element is received by the first collar.

In some embodiments, decoupling the first coupling element from the second collar permits the second coupling element to be decoupled from the first collar.

In some embodiments, the first collar is biased to rotate relative to the housing by a biasing means, such as a spring; and the first collar is arrangeable relative to the housing in a first rotational position and a second rotational position, wherein the first collar is biased towards the second rotational position by the biasing means; and the fluid contained in the cavity is configured to impede rotational movement of the first collar from the first rotational position into the second rotational position, to slow down the speed at which the first collar rotates relative to the housing.

In some embodiments, the first coupling element comprises a flexible, deformable or deflectable element.

In some embodiments, the first coupling element comprises a cantilevered arm.

In some embodiments, the cantilevered arm has a fixed end and a free end.

In some embodiments, the free end is configured to be deformable, deflectable, or otherwise displaceable relative to the fixed end, for example upon application of a force to the free end.

In some embodiments, movement of a plunger of a medicament delivery device is configured to cause a force to be applied to the free end of the cantilevered arm.

In some embodiments the free end comprises a clip element.

In some embodiments, the free end is configured to be received in a receiving portion of the second collar.

In some embodiments, the receiving portion of the second collar comprises a recess, channel, aperture or groove, which may be oriented to be generally parallel to the central longitudinal axis.

In some embodiments, removal of the free end of the first coupling element from the receiving portion of the second collar causes the first collar to rotate relative to the housing and relative to the second collar.

In some embodiments, the second coupling element is configured to protrude from a main body of the second collar, generally along a radial direction that is generally normal to the central longitudinal axis.

In some embodiments, the first collar comprises a receiving element configured to receive the second coupling element.

In some embodiments, rotation of the first collar relative to the housing and relative to the second collar causes the second coupling element to become decoupled from the receiving element of the first collar.

In some embodiments, rotation of the first collar relative to the second collar permits the second collar to move axially relative to the first collar along the longitudinal direction.

In some embodiments, the receiving element of the first collar comprises a recess, channel, aperture or groove, which may be oriented to be generally normal to the central longitudinal axis.

In some embodiments, the damping device is configured to provide a time delay between the change of state of one part and the triggering of another mechanism in a medicament delivery device.

In some embodiments, rotational movement of the first collar relative to the housing is configured to trigger said mechanism, and the fluid is configured to slow down the rotational speed of the first collar relative to the housing in order to provide said time delay.

In some embodiments, the damping device is configured to provide a time delay between the change of state of a plunger of a medicament delivery device and the triggering of a needle retraction mechanism of the medicament delivery device.

In some embodiments, the damping device according to the first aspect of this disclosure is configured for use with or in a medicament delivery device comprising any one or more of the features described below in relation to the second aspect of this disclosure.

A second aspect of this disclosure provides a medicament delivery device comprising a damping device according to the first aspect of this disclosure.

In some embodiments, the damping device comprises any one or more of the features described above in relation to the first aspect of this disclosure.

In some embodiments, the medicament delivery device further comprises a body having a proximal end and a distal end; a needle for injecting medicament into a user, wherein the needle is movable relative to the body from a pre-use position to an injecting position, wherein in the pre-use position the distal end of the needle is arranged within the body, and in the injecting position the distal end of the needle protrudes outside of the distal end of the body for injecting medicament into the user; and a plunger moveable relative to the body along the central longitudinal axis towards the distal end of the body from a first position to a second position, wherein movement of the plunger from the first position into the second position causes the needle to move from the pre-use position into the injecting position; wherein when the plunger is moved from the first position to the second position, the first collar is caused to rotate relative to the housing from a first rotational position into a second rotational position; wherein movement of the first collar from the first rotational position into the second rotational position is impeded by the fluid in the cavity; and wherein when the first collar reaches the second rotational position, the plunger is caused to move along the central longitudinal axis towards the proximal end of the body.

In some embodiments, the medicament delivery device also comprises a spring carrier configured to house at least a portion of the spring, and/or a spring guide configured to guide and/or constrain the movement of the spring.

In some embodiments, the spring guide is generally cylindrical.

In some embodiments, the medicament delivery device is configured to be arranged in a pre-use state, in which the plunger is in the first position, and the second collar is coupled to the first collar, such that the second collar is axially and rotationally fixed relative to the first collar.

In some embodiments, when the medicament delivery device is in the pre-use state, the second collar is configured to be coupled to the first collar by one or more coupling elements.

In some embodiments, when the medicament delivery device is in the pre-use state, the second collar is configured to be coupled to the first collar by a first coupling element and a second coupling element.

In some embodiments, the first collar comprises the first coupling element.

In some embodiments, the first coupling element comprises a flexible, deformable or deflectable element.

In some embodiments, the first coupling element comprises a cantilevered arm.

In some embodiments, the cantilevered arm has a fixed end and a free end.

In some embodiments, the free end is configured to be deformable, deflectable, or otherwise displaceable relative to the fixed end.

In some embodiments the free end comprises a clip element.

In some embodiments, the free end is configured to be received in a receiving portion of the second collar.

In some embodiments, the receiving portion of the second collar comprises a recess, channel, aperture or groove, which may be oriented to be generally parallel to the central longitudinal axis.

In some embodiments, the second collar comprises the second coupling element.

In some embodiments, the second coupling element is configured to protrude from a main body of the second collar, generally along a radial direction that is generally normal to the central longitudinal axis.

In some embodiments, the first collar comprises a receiving element configured to receive the second coupling element.

In some embodiments, the receiving element of the first collar comprises a recess, channel, aperture or groove, which may be oriented to be generally normal to the central longitudinal axis.

In some embodiments, the medicament delivery device comprises a medicament.

According to another aspect of the present disclosure there is provided a method of manufacturing or assembling a medicament delivery device, wherein the medicament delivery device is defined in claim 1. Further optional features of the medicament delivery device are described and/or contemplated here.

According to another aspect of the present disclosure there is provided a method of manufacturing or assembling a medicament delivery device, wherein the medicament delivery device has the features of any of the medicament delivery devices described and/or contemplated herein.

BRIEF DESCRIPTION OF THE DRAWINGS

Embodiments will now be described, by way of example only, with reference to the accompanying drawings, in which:

FIG. 1A shows a schematic view of a medicament delivery device with a cap attached;

FIG. 1B shows a schematic view of the medicament delivery device of FIG. 1A with the cap removed;

FIG. 2A is a schematic view of a medicament delivery device prior to use (i.e. in a pre-use configuration);

FIG. 2B is a schematic view of the device of FIG. 2A with the cap removed;

FIG. 2C is a schematic view of the device of FIG. 2A showing the device placed at an injection site;

FIG. 2D is a schematic view of the device of FIG. 2A with the button having been pressed to release the dispensing mechanism;

FIG. 5A shows a cross-sectional schematic view of a portion of a medicament delivery device including a damping device;

FIG. 5B shows a cross-sectional schematic view of a portion of a medicament delivery device including a damping device;

FIG. 5C shows a cross-sectional schematic view of a portion of a medicament delivery device including a damping device;

FIG. 5D shows a cross-sectional schematic view of a portion of a medicament delivery device including a damping device;

FIG. 8 shows a cross-sectional schematic view of a damping device comprising a radial sealing arrangement;

FIG. 9 shows a cross-sectional schematic view of a damping device comprising a radial sealing arrangement;

FIG. 10 shows a cross-sectional schematic view of a damping device comprising a radial sealing arrangement;

FIG. 11 shows a cross-sectional schematic view of a damping device comprising a radial sealing arrangement;

DETAILED DESCRIPTION

Figure 2G:
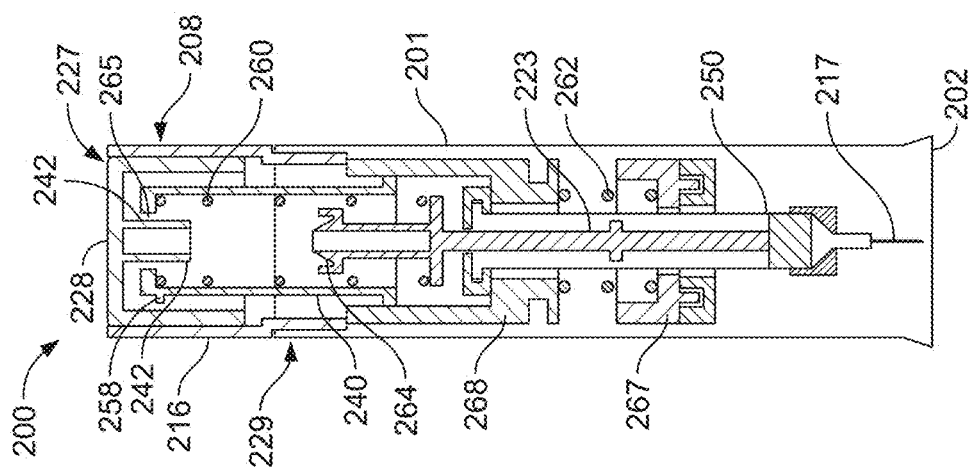
FIG. 2G is a schematic view of the device of FIG. 2A showing the device removed from the injection site after the needle has retracted within the device after delivery of the medicament.

A drug delivery device (also referred to as an injection device), as described herein, may be configured to inject a medicament into a subject such as a human or animal. For example, delivery could be sub-cutaneous, intra-muscular, or intravenous. Such a device could be operated by a user, who may or may not be the subject. In examples where the user is not the subject, the user may be a care-giver such as a nurse or physician. The device can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a subject's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors such as a drug ranging in viscosity from about 3 cP to about 50 cP. Consequently, a drug delivery device will often include a hollow needle ranging from about 25 to about 31 Gauge in size. Common sizes are 27 and 29 Gauge.

The dispensing mechanism provides one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

The medicament delivery device can include various types of safety syringe, pen-injector, or auto-injector. The device can include a cartridge-based system that requires piercing a sealed ampule before use.

Distal movement of the actuation member may cause automatic dispensing of the medicament from the device and/or distal movement of the actuation member may cause the distal movement of the needle from a needle pre-use position to a needle injection position. The dispensing mechanism may be configured to dispense medicament from the needle when the dispensing mechanism is released.

In the needle pre-use position the needle may be flush with the distal end of the body or the needle may be recessed within the body. In another embodiment the needle may be fixed in position relative to the body.

In another device, different features may be provided to prevent the actuation member from moving distally. For example, the stop may be provided on another component of the medicament delivery device. In another device a lock ring 216 is not present.

According to some embodiments of the present disclosure, an exemplary drug delivery device 10 is shown in FIGS. 1A & 1B. The device 10, as described above, is configured to inject a medicament into a patient's body. The device 10 includes a housing 11 which typically contains a reservoir containing the medicament to be injected (e.g., a syringe) and the components required to facilitate one or more steps of the delivery process. The device 10 can also include a cap assembly 12 that can be detachably mounted to the housing 11. A user typically removes the cap 12 from the housing 11 before the device 10 is operated. As shown, the housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site. The device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from distal region 20 of housing 11. Insertion of the needle 17 can occur via several mechanisms. For example, the needle 17 may be fixedly located relative to the housing 11 and initially be located within an extended needle sleeve 13. Proximal movement of the sleeve 13 by placing a distal end of the sleeve 13 against a patient's body and moving the housing 11 in a distal direction will uncover the distal end of the needle 17. Such relative movement allows the distal end of the needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to the housing 11. Such insertion can be triggered by movement of the sleeve 13 or by another form of activation, such as, for example, a button 22. As shown in FIGS. 1A & 1B, the button 22 is located at a proximal end of the housing 11. However, in other embodiments, the button 22 could be located on a side of the housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through the needle 17. In some embodiments, a drive spring (not shown) is under compression before the device 10 is activated. A proximal end of the drive spring can be fixed within proximal region 21 of the housing 11, and a distal end of the drive spring can be configured to apply a compressive force to a proximal surface of the piston 23. Following activation, at least part of the energy stored in the drive spring can be applied to the proximal surface of the piston 23. This compressive force can act on piston 23 to move it in a distal direction. Such distal movement acts to compress the liquid medicament within the syringe, forcing it out of the needle 17. Following injection, the needle 17 can be retracted within the sleeve 13 or the housing 11. Retraction can occur when the sleeve 13 moves distally as a user removes the device 10 from a patient's body. This can occur as the needle 17 remains fixedly located relative to the housing 11. Once a distal end of sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe to move it in a proximal direction. Following sufficient retraction, any relative movement between the needle 17 and the housing 11 can be locked with a locking mechanism. In addition, the button 22 or other components of the device 10 can be locked as required.

FIGS. 2A to 2G show the sequential steps of operating a medicament delivery device 200. The medicament delivery device 200 is an autoinjector.

The device 200 comprises a body 201, a syringe 250 having a needle 217 and an axially moveable plunger 223 for dispensing medicament from the syringe 250. The device comprises a cap 254 which is removably attached to the body 201 and covers a distal end 202 of the body 201 for preventing access to the needle 217. The device has a needle shield 266 that covers the needle 217 before use. The needle shield 266 is attached to the cap 254.

The medicament delivery device 200 has a dispensing mechanism 229. The medicament delivery device 200 has an actuation member 227 which is configured to release the dispensing mechanism 229. The actuation member 227 is configured to engage the dispensing mechanism 229 to release the dispensing mechanism 229.

The dispensing mechanism 229 is configured to cause the needle 217 to move distally from a needle pre-use position, in which the needle 217 is recessed within the body 201, to an injection position in which the needle 217 protrudes from the distal end 202 of the body 201 when the dispensing mechanism 229 is released.

The dispensing mechanism 229 is configured to dispense the medicament from the needle 217 when the needle 217 is in the injection position.

As shown in FIGS. 2B-2C, in order to deliver a dose of medicament to an injection site, the cap 254 is removed (FIG. 2B) and the device is placed at an injection site 232 (FIG. 2C).

The actuation member 227 comprises a button 228 and is prevented from being depressed by a stop 258. The stop is provided on the spring guide 240, for example.

The device has a locking member 208 in the form of a lock ring 216 which is rotatable by a user about a longitudinal axis of the device. The actuation member 227 is keyed to the lock ring 216 so that the actuation member 227 rotates with the lock ring 216. The lock ring 216 is rotatable from a pre-use position, in which distal movement of the button 228 is prevented, to a use position in which distal movement of the button 228 is permitted.

When the lock ring 216 is in the pre-use position then the stop 258 engages the button 228 to prevent the button 228 from being depressed.

In order to allow the button 228 to be depressed, the lock ring 216 is rotated about the longitudinal axis of the device from the pre-use position to the use position. The rotation of the lock ring 216 also rotates the actuation member 227 to a position in which the stop 258 no longer prevents the button 228 from being depressed as shown, for example, in FIG. 2C.

Turning now to FIG. 2D, the user then presses the button 228 to release the dispensing mechanism 229 for dispensing medicament from the device. The dispensing mechanism 229 has a plunger 223 and a bias in the form of a compression spring 260. The plunger 223 is biased distally by the spring 260.

The dispensing mechanism 229 is at least partially housed within the spring guide 240. The plunger 223 has a release member which has proximally-extending clips 264. The spring 260 is retained in the compressed position by virtue of the clips 264 which protrude through a proximal opening 265 in the spring guide 240. The clips 264 engage the spring guide 240 for maintaining the plunger 223 in a proximal position.

The actuation member 227 has a firing member comprising a pair of protrusions 242 which engage with the clips 264 when the button 228 is depressed to flex the clips 264 radially inwardly thereby allowing the clips 264 to move distally through the proximal opening 265 to release the spring 260.

When the dispensing mechanism 229 is released, then the syringe 250 is released for distal axial movement towards the injection site 232 such that the needle 217 moves from the needle pre-use retracted position to an exposed (or "uncovered" or "injection") position for delivering medicament to the injection site 232 under the biasing force of the compression spring 260.

Figure 2F:
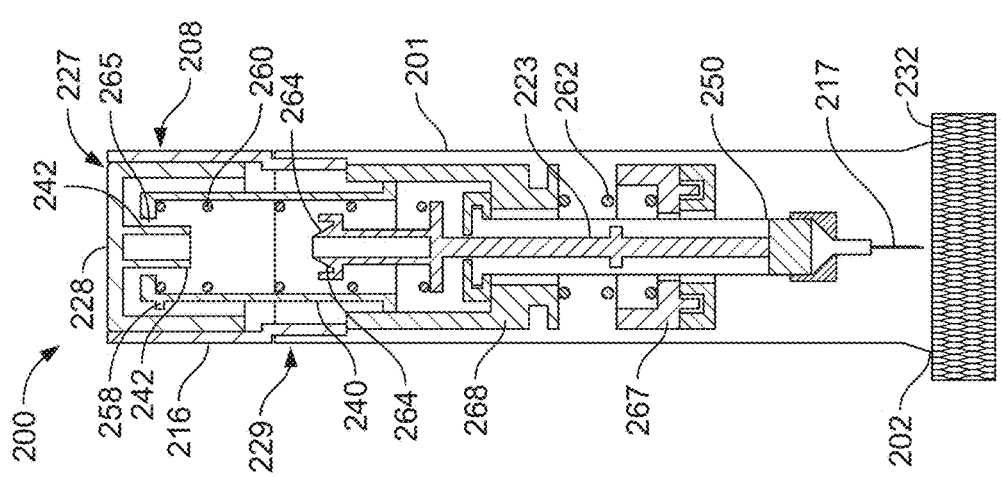
FIG. 2F is a schematic view of the device of FIG. 2A showing the needle having retracted within the device after a dose has been delivered.
Figure 2E:
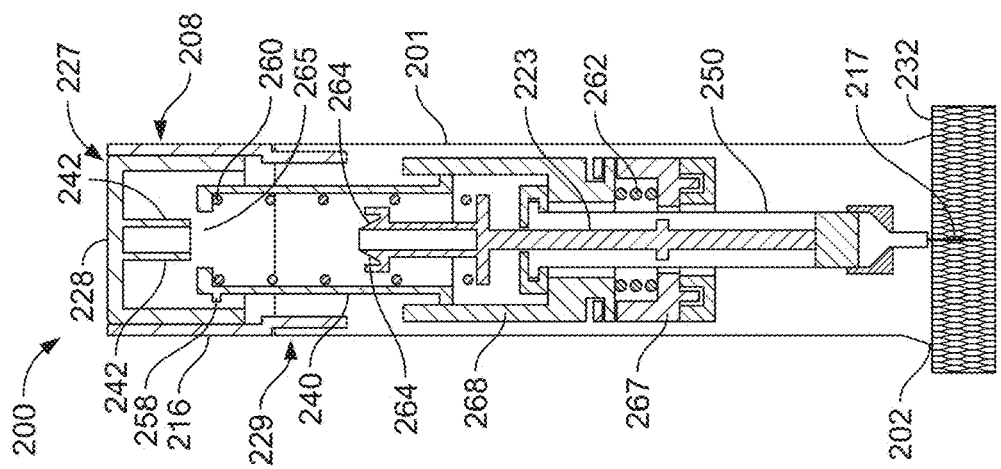
FIG. 2E is a schematic view of the device of FIG. 2A with the button having been pressed to release the dispensing mechanism.

Depressing the button 228 releases the plunger 223 which, biased by the bias 260, moves along the syringe 250 towards the distal end of the device 200 to force medicament within the syringe 250 through the needle 217, thereby delivering a dose of medicament as shown, for example in FIG. 2E.

As shown in FIG. 2F, once the dose of medicament has been delivered, a medicament container bias 262, embodied by a further spring 262, then causes the needle 217 to move axially back to the retracted position, away from the injection site 232 in a proximal direction. The plunger 223 flexes a clip (not shown) on a first collar 267 which allows the first collar 267 to rotate relative to the body 201 and relative to a second collar 268. The first collar 267 rotates from a first position in which the second collar 268 is axially coupled to the first collar 267, into a second position in which the second collar 268 is free to move axially relative to the first collar 267. For example, the second collar 268 may comprise a radially protruding coupling element configured to be received in or engage with a corresponding receiving portion of the first collar 267, such that rotating the first collar 267 from the first position into the second position causes the coupling element to be moved out from the receiving portion, to allow the second collar 268 to move axially relative to the first collar 267. Axial movement of the second collar 268 permits the needle 217 to be retracted. As shown in FIG. 2G, the device 200 is then removed from the injection site 232, for disposal.

The medicament delivery devices described herein may have some or all of the features as described in relation to the medicament delivery device 200.

The dispensing mechanism 229 may have the some or all of the features as described and/or contemplated in relation to FIGS. 2A to 2G.

In another embodiment, the dispensing mechanism may have alternative or additional features to those described and/or contemplated in relation to FIGS. 2A to 2G. The dispensing mechanism may have features as described and/or contemplated herein, for example in relation to FIGS. 1A and 1B.

Figure 3:
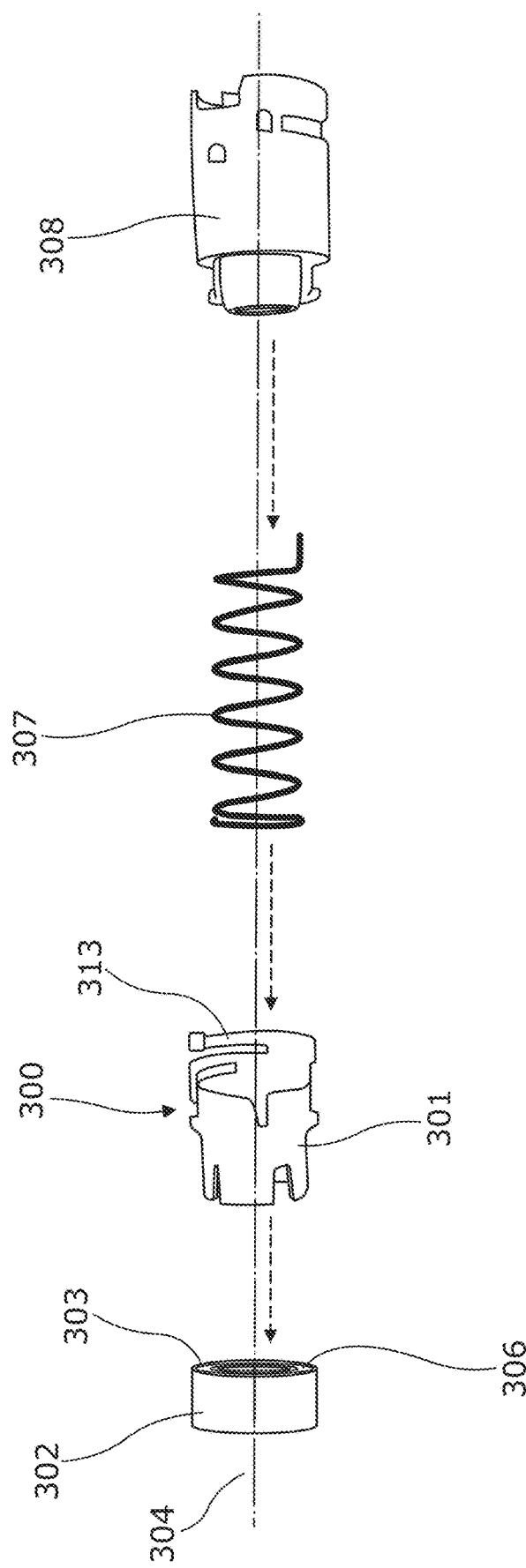
FIG. 3 shows an exploded view of an unassembled damping device.

FIG. 3 shows an exploded view of the components of an exemplary damping device 300 for a medicament delivery device 200 in an unassembled state, which may be employed in, for example, a medicament delivery device 200 as described above and shown in FIGS. 1A to 2G. In the examples described herein, the medicament delivery device 200 comprises the damping device 300, although it is also envisaged that the damping device 300 may also be configured to be an add-on device to be fitted to a medicament delivery device 200. The function of the damping device 300 in the medicament delivery device 200 is to provide a time delay between the change of state of one part, for example a plunger 223, 309, and the triggering of another mechanism. For example, to provide a time delay between a plunger 223, 309 reaching a certain position and the triggering of a needle 217 retraction mechanism. This may be achieved by the damping device 300 being configured to slow down or impede the movement of one or more parts of the medicament delivery device 200, to act as a damper thereto.

The damping device 300 comprises a housing 302, a first collar 301, a second collar 308, and a spring 307. In the example shown, the housing 302, the first collar 301 and the second collar 308 are each shown to be generally cylindrical, although it is also envisaged that the housing 302, the first collar 301 and the second collar 308 may have any other suitable shape or form. The housing 302, the first collar 301 and the second collar 308 are configured to be assembled with one another such that they are arranged concentrically with one another about a longitudinal axis 304 of the damping device 300, and to be slidably received with one another. For example, the housing 302 may be configured to receive a first portion of the first collar 301 and the second collar 308 may be configured to receive a second portion of the first collar 301. The first collar 301 is configured to be rotationally movable relative to the housing 302 and relative to the second collar 308 about the longitudinal axis 304. The first collar 302 is biased to rotate relative to the housing by the spring 307, which serves as a biasing means.

Figure 4D:
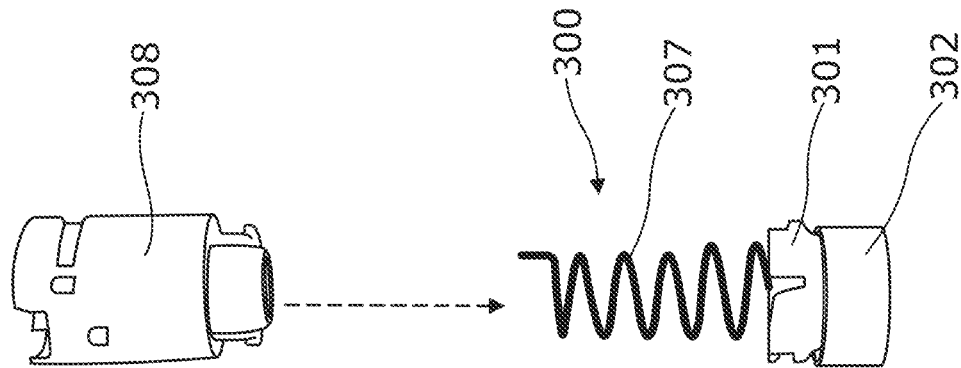
FIG. 4D shows a housing, a first collar, a spring, and a second collar.
Figure 4C:
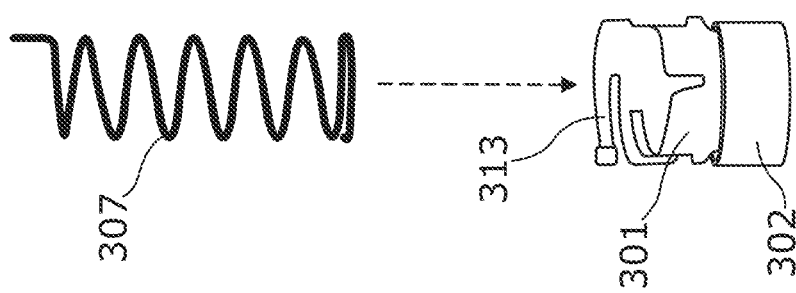
FIG. 4C shows a housing, a first collar, and a spring.
Figure 4B:
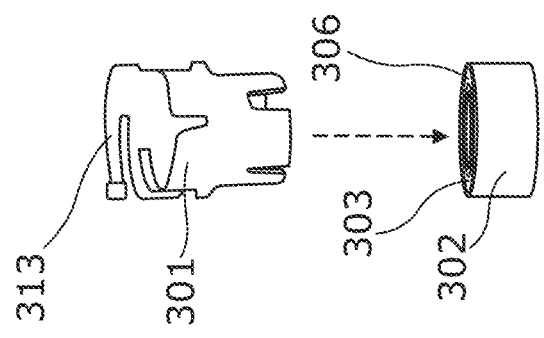
FIG. 4B shows a housing and a first collar.
Figure 4A:
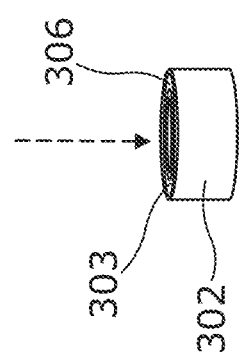
FIG. 4A shows a housing.

FIGS. 4A to 4D sequentially show the steps of an exemplary method of assembling the damping device 300. FIG. 4A shows the housing 302. FIG. 4B shows the housing 302 and the first collar 301. As shown sequentially between FIGS. 4B and 4C, the housing 302 and the first collar 301 may be assembled together by moving the first collar 301 along the longitudinal axis 304 towards the housing 302 such that at least a portion of the first collar 301 is concentrically received in the housing 302. Next, as shown sequentially between FIGS. 4C and 4D, the spring 307 may be assembled together with the housing 302 and the first collar 301 by similarly assembling it along the longitudinal axis 304. Next, the second collar 308 may be moved along the longitudinal axis 304 from the position shown in FIG. 4D, to assemble it together with the housing 302, the first collar 301 and the spring 307. The operation of the damping device 300 shall now be described in the context of the medicament delivery device 200, with reference to FIGS. 5A to 5D.

FIG. 5A shows the damping device 300 as assembled in a medicament delivery device 200. Purely for illustrative purposes, the housing 302 and the spring 307 are not shown. The medicament delivery device comprises a plunger 309, which may be substantially similar to the plunger 223 described above and shown in FIGS. 2A to 2G, and a body 332, which may be substantially similar to the body 201 described above and shown in FIGS. 2A to 2G. The plunger 309 is configured to be movable relative to the body 332 along a longitudinal direction 312 from a first position (see FIG. 5A) to a second position (see FIG. 5B), wherein movement of the plunger 309 from the first position into the second position causes the needle 217 (not shown) of the medicament delivery device 200 to be moved from a pre-use position into an injecting position. In the pre-use position, a distal end of the needle 217 is arranged within the body 332, and in the injecting position the distal end of the needle 217 protrudes outside of the distal end 202 of the body 332 for injecting medicament into a user. The medicament delivery device 200 also comprises a spring carrier 310 configured to house the spring 307, and a spring guide 311 configured to guide and/or constrain the movement of the spring 307. The damping device 300 is configured to delay movement of the plunger 309 from the second position (see FIG. 5B) into a post-use position, in order to provide a time delay so that the needle 217 is not automatically retracted until the full dose of medicament has definitely been dispensed from the needle 217, as described below.

FIG. 5A shows the medicament delivery device 200 in a pre-use state, in which the plunger 309 is in the first position in which the needle 217 is in a retracted, pre-use state. In this state, the second collar 308 is coupled to the first collar 301, such that the second collar 308 is axially and rotationally fixed relative to the first collar 301. That is, in the pre-use state, the first and second collars 301, 308 cannot move relative to one another rotationally about the longitudinal axis 304, or move axially relative to one another along the longitudinal direction 312. The second collar 308 is coupled to the first collar 301 via a first coupling element 313 and a second coupling element 315. The first collar 301 comprises the first coupling element 313 which in the example shown, is in the form of a cantilevered arm 313. The cantilevered arm 313 has a fixed end 316 and a free end 317, and the free end 317 is configured to be deformable, deflectable, or otherwise displaceable from the fixed end 316. The free end 317 comprises a clip element. The free end 317 of the cantilevered arm 313, and in particular, the clip element thereof, is configured to be received in a receiving portion 333 of the second collar 308, which may comprise a recess, channel, aperture or groove oriented to be generally parallel to the longitudinal direction 312. The second collar 308 comprises the second coupling element 315, which in the example shown, is arranged to protrude from a main body of the second collar 308, generally along the radial direction which is generally normal to the longitudinal direction 312. The first collar 301 comprises a corresponding receiving element 314 configured to receive the second coupling element 315. The receiving element 314 may comprise a recess, channel, aperture or groove oriented to be generally normal to the longitudinal direction 312.

Thus, as shown in FIG. 5A, in the pre-use state, the first and second collars 301, 308 are coupled to one another such that the first collar 301 is constrained from rotating relative to the body 332 and relative to the second collar 308, and such that the second collar 308 is constrained from moving axially relative to the first collar 301 along the longitudinal direction 312. Next, in order to prepare the medicament delivery device 200 for medicament injection, the plunger 309 may be moved into the second position along the distal direction as described above in relation to FIGS. 2A to 2G in order to place the needle 217 into the injection position. Movement of the plunger 307 into the second position causes the plunger 307 to apply a force to the clip element, thus exerting a force on the free end 317 of the cantilevered arm 313, which causes the free end 317 to flex or otherwise deform relative to the fixed end 316. As shown sequentially between FIGS. 5B and 5C, this causes the clip element to be pushed out of the receiving portion 333 such that it is no longer received in and constrained by the second collar 308, into the position shown in FIG. 5C. In this position, the first collar 301 is no longer rotationally constrained relative to the second collar 308 and the body 332, and because the first collar 301 is biased to rotate relative to the body 332 by the spring 307 as described above, removal of the clip element from the receiving portion 333 thus causes the first collar 301 to rotate relative to the body 332 and the second collar 308. This is automatically actuated by movement of the plunger 309 from the position shown in FIG. 5A into the position shown in FIG. 5C.

Next, as shown in FIG. 5C, the first collar 301 is thus automatically caused to rotate relative to the body 332 and relative to the second collar 308, by the biasing action of the spring 307, along the rotational direction shown by the arrow 334, which causes the receiving element 314 of the first collar 301 to be moved out from alignment with the second coupling element 315 of the second collar 308. This causes the second collar 308 to become decoupled from the first collar 301 and whilst the first collar 301 is now permitted to rotate relative to the second collar 308, this also permits the second collar 308 to move axially along the longitudinal direction 312 relative to the first collar 301. As shown in FIG. 5D, axial movement of the second collar 308 along the longitudinal direction 312 towards the proximal end 203 of the body 332 causes the plunger 309 and the spring 310 to also move along the longitudinal direction 312 towards the proximal end 203, together with the second collar 308, away from the first collar 301. It may be desirable for the medicament delivery device 200 to be placed into this state post-injection, i.e. after the full dose of a medicament has been dispensed from the needle 217, in order to retract the needle 217 inside the body 332, for hygiene and safety reasons. In the example shown, retracting the needle 217 requires the plunger 209 to be retracted relative to the body 332. In the position shown in FIG. 5B, the coupling of the second collar 308 to the first collar 301 prevents the plunger 209 from being retracted back towards the proximal end 203 of the body 332, but when the second collar 308 is released from the first collar 301 axially, caused by the rotation of the first collar 301 relative thereto, then the plunger 209 is no longer constrained from being retracted back towards the proximal end 203 of the body 332, and can thus move into the position shown in FIG. 5D. In the position shown in FIG. 5D, a clip element 318 of the spring carrier 310 may be configured to snap into a recess in the spring guide 311, thus preventing needle 217 and the pre-filled syringe from being exposed again, for example by the plunger 309 moving back along the distal direction again, and making the medicament delivery device 200 needle safe. This may also provide an end of dose click to provide audible feedback to the user that medicament delivery has been completed.

There may be a need within the medicament delivery device 200 to create a time delay between the change of state of the plunger 209 reaching the second position and the triggering of the needle 217 retraction mechanism and/or end of dose feedback to the user. For example, after all the medicament has been delivered from the needle 217, it may be desirable to retract the needle 217 and/or for the user to be given feedback, for example audible and/or visual and/or tactile feedback, that the medicament has been delivered in full. It may be desirable that the needle 217 should not be retracted and/or end of dose feedback should not be given before the end of the dose has been reached, i.e. before the full dose of medicament has been delivered. However, due to part tolerances for example, it may not be possible to instantaneously trigger needle 217 retraction at the exact point in time that end of dose is reached, as this may risk needle 217 retraction not being triggered. Furthermore, if the needle 217 is retracted as soon as the plunger 309 reaches the end of dose, there may be a risk that not all of the fluid will have been delivered to the patient through the needle 217. If there is no time delay, there is thus a risk that the needle 217 be retracted and/or end of dose feedback is given, before all the drug has been delivered. Providing a suitably long time delay between the end of dose delivery and the needle 217 retraction and/or end of dose feedback may advantageously avoid these issues. The damping device 300 may advantageously provide such a time delay to add a time delay between the plunger 309 reaching the second position (corresponding with the dose of medicament having been delivered in full via the needle 217) and the needle retraction energy being released, to cause the needle 217 to automatically be retracted. The damping device 300 provides such a time delay by providing a time delay to the rotational movement of the first collar 301 relative to the body 332 and to the second collar 308, i.e. by slowing down the rotational movement of the first collar 301 from the position shown in FIG. 5B into the position shown in FIG. 5C. In the position shown in FIG. 5B, the second coupling element 315 of the second collar 308 is still received in the receiving element 314 of the first collar 301, so axial movement of the second collar 308 and hence correspondingly along the plunger 309 is still prevented. However, in the position shown in FIG. 5C, the second coupling element 315 is released so that the second collar 308 is axially freed, allowing the plunger 309 to move back into a retracted position. To move between these two stages requires rotation of the first collar 301, hence by slowing down the rotational movement of the first collar 301, the time between these two stages can be delayed and hence controlled.

Turning back now to FIGS. 4A to 4D, the exemplary damping device 300 achieves this slowing down of the rotation of the first collar 301 by impeding the rotational movement of the first collar 301 relative to the housing 302, the housing 302 remaining rotationally fixed relative to the body 332. The housing 302 comprises a generally annular cavity, i.e. a generally ring shaped cavity, comprising an inner surface 320 and an outer surface 321 (see FIG. 6 for example). The cavity 303 comprises an open end 306 into which the first collar 301 is configured to be inserted. The cavity 303 is configured to receive the first collar 301 such that as shown in FIGS. 4C and 4D, a first portion of the first collar 301 is arranged within the cavity 303, to be circumferentially concentrically received in and circumscribed by the housing 302, and a second portion of the first collar 301 is arranged to protrude from the housing 302. The first collar 301 is rotatable within the cavity 303 about the longitudinal axis 304 relative to the housing 302.

Figure 6:
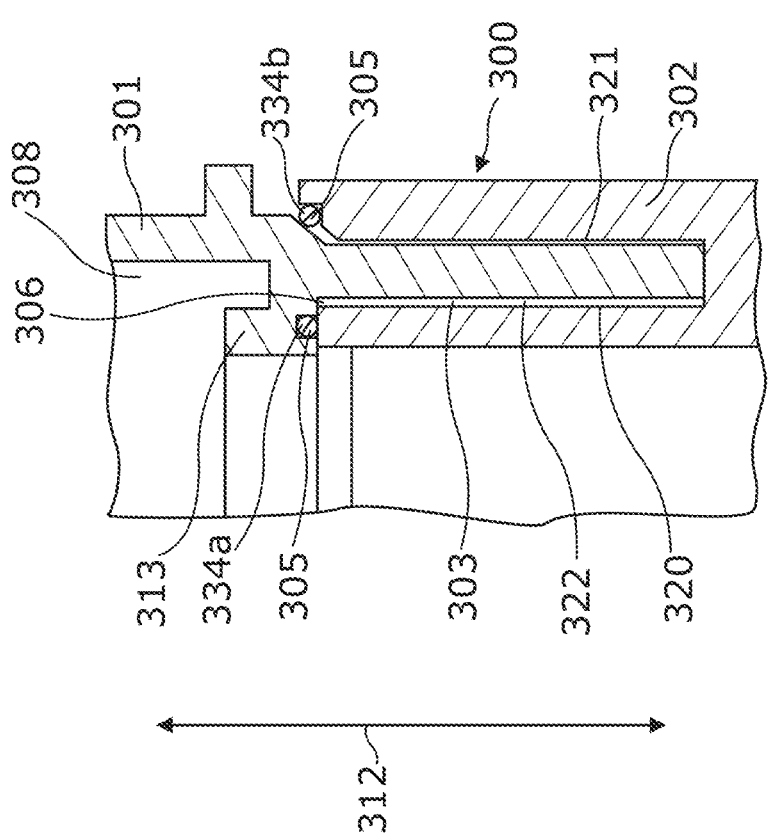
FIG. 6 shows a cross-sectional schematic view of a damping device comprising an axial sealing arrangement.

The cavity 303 has an inner radius and an outer radius defined by the inner surface 320 and the outer surface 321 respectively, and the thickness of the cavity 303 is defined as the difference between the outer radius and the inner radius. That is, in a plane that is generally normal to the longitudinal axis 304, the cavity 303 has a generally annular cross-sectional profile, and the thickness of the cavity 303 is defined as the thickness of the annulus. The thickness of the cavity 303 is larger than the wall thickness of the first portion of the first collar 301 which is configured to be received in the housing 302, such that when the first collar 301 is received in the cavity 303, there is a gap 322 between the first collar 301 and the inner and/or outer surfaces 320, 321 of the cavity 303, for example as shown in FIG. 6. That is, when the first collar 301 is received in the cavity 303, the first collar 301 is spaced apart from the inner surface 320 and/or the outer surface 321, such that a gap 322 is provided within the cavity 303 adjacent to the first collar 301. The cavity 303 is configured to contain a fluid, for example grease, in the gap 322, for impeding rotational movement of the first collar 301 relative to the housing 302. That is, fluid in the cavity 303 is configured to slow down the rotation of the first collar 301 in the cavity 303, thus acting to damp the first collar's 301 rotation. In this manner, the rotation of the first collar 301, and hence the automatic triggering of the needle retraction mechanism, can be provided with a time delay as described above. The housing 302 may be filled with grease, or another suitable fluid to provide a damping effect, before the first collar 301 is inserted into the housing 302, for example the housing 302 may be filled with grease in the state shown in FIG. 4A. Exemplary ways in which the fluid can be prevented from leaking out of the cavity 303 of the housing 302 shall now be described, with reference to FIGS. 6 to 12, which show damping devices 300 each comprising a sealing arrangement 305 configured to fluidly seal an interface between the housing 302 and the first collar 301, for example an interface at the open end 306 of the cavity 303.

The sealing arrangement 305 may comprise an axial seal arranged to fluidly seal the interface between the housing 302 and the first collar 301 along a longitudinal direction 312 that is generally parallel to the longitudinal axis 304 of the damping device 300. Exemplary axial sealing arrangements 305 are shown in FIG. 6. In the example shown in FIG. 6, the sealing arrangement 305 comprises a first O-ring 334a and a second O-ring 334b. The first O-ring 334a is arranged proximate to the inner surface 320 of the cavity 303, and the second O-ring 334b is arranged proximate to the outer surface 321 of the cavity 303. Both the first and second O-rings 334a, 334b are arranged axially between the housing 302 and the first collar 301. That is, along the longitudinal direction 312, they are arranged between the housing 302 and the first collar 301, such that they axially seal the interface between the housing 302 and the first collar 301, to fluidly seal the open end 306 of the cavity 303, in order to prevent the fluid from inadvertently leaking out of the cavity 303. Whilst in the example shown in FIG. 6, there are two O-rings 334a, 334b, it is also envisaged that there may be just one O-ring present. For example, there may be just a first O-ring 334a arranged proximate to the inner surface 320 of the cavity 303, or there may be just a second O-ring 334b arranged proximate to the outer surface 321 of the cavity 303. It is also envisaged that there may be any other number of O-rings, for example three or more O-rings. Furthermore, whilst in the example shown each of the O-rings 334a, 334b has a generally circular cross-sectional profile, each of the one or more O-rings 334a, 335b may have any other suitable cross-sectional profile, such as a generally quadrilateral or triangular cross-sectional profile. The O-rings may be formed from an elastomeric material, such as silicone, viton, ethylene propylene diene monomer, or nitrile rubber for example.

Figure 7:
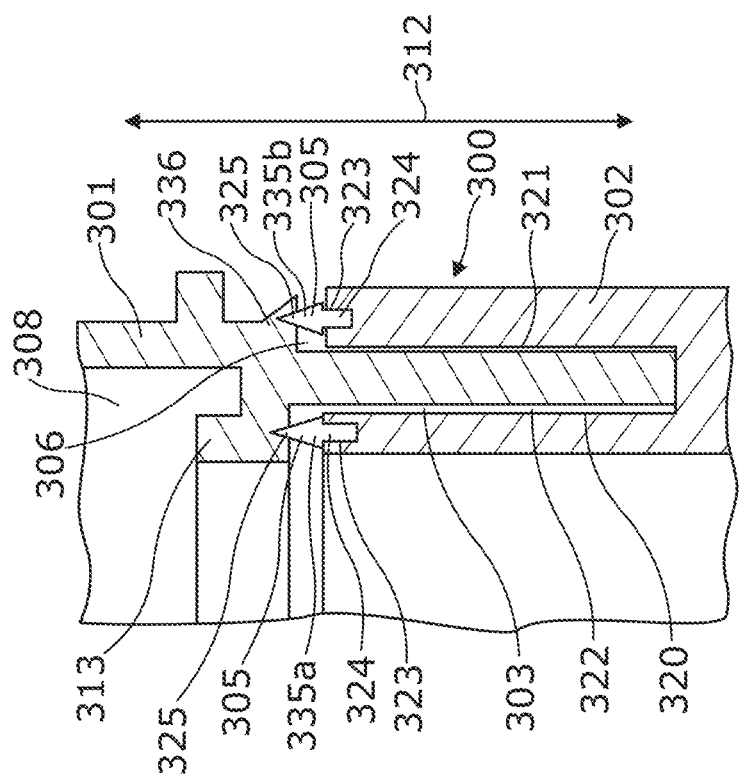
FIG. 7 shows a cross-sectional schematic view of a damping device comprising an axial sealing arrangement.

In the example shown in FIG. 7, the damping device 300 is substantially similar to that shown in FIG. 6 and described above, albeit instead of comprising O-rings 334a, 334b, the sealing arrangement 305 comprises a first seal 335a and a second seal 335b. The first seal 335a is arranged proximate to the inner surface 320 of the cavity 303, and the second seal 335b is arranged proximate to the outer surface 321 of the cavity 303. Both the first and second seals 335a, 335b are arranged axially between the housing 302 and the first collar 301. That is, along the longitudinal direction 312, they are arranged between the housing 302 and the first collar 301, such that they axially seal the interface between the housing 302 and the first collar 301, to fluidly seal the open end 305 of the cavity 303, in order to prevent the fluid from inadvertently leaking out of the cavity 303. Each of the seals 335a, 335b may be generally annular. Whilst in the example shown in FIG. 7, there are two seals 335a, 335b, there may be just a first seal 335a arranged proximate to the inner surface 320 of the cavity 303, or there may be just a second seal 335b arranged proximate to the outer surface 321 of the cavity 303. It is also envisaged that there may be any other number of seals 335a, 335b, for example three or more seals.

In the example shown, each of the seals 335a, 335b comprises a generally arrow shaped cross-sectional profile, and is configured to be overmolded, for example formed from an elastomeric material such as silicone, viton, ethylene propylene diene monomer, or nitrile rubber for example, onto the housing 302. The housing 302 comprises a pair of generally annular recesses 323, one arranged proximate to the inner surface 320 of the cavity 303 and the other arranged proximate to the outer surface 321 of the cavity 303, which are each configured to receive a respective one of the overmolded first and second seals 335a, 335b. In particular, each of the first and second seals 335a, 335b comprises a coupling portion 324 which is arranged to protrude into and be received in a respective one of the recesses 323, and which in the example shown, has a generally rectangular cross-sectional profile. Each of the first and second seals 335a, 335b also comprises a sealing portion 325 integrally formed with the coupling portion 324 and arranged to protrude therefrom and out away from the respective recess 323, towards the first collar 301, in order to seal the interface between the first collar 301 and the housing 302 in the longitudinal direction 312. In the example shown, each of the sealing portions 325 has a generally triangular cross-sectional profile, such that each of the seals 335a, 335b has a generally arrow shaped cross-sectional profile. In the example shown, the two seals 335a, 335b are substantially identical in shape in that they both have the same cross-sectional profile, however it is also envisaged that the two seals 335a, 335b may have different cross-sectional profiles, for example different shapes and/or sizes, and that one or more of the seals 335a, 335b need not necessarily have an arrow shaped cross-sectional profile, but that any other suitable shape or form may also be employed. It is also envisaged that the seals 335a, 335b need not necessarily be overmolded onto the housing 302, but may otherwise be coupled to or integrally formed with the housing 302. The shape of the first collar 301 may be designed accordingly to fit with the seals 335a, 335b. For example, the first collar 301 may comprise an interfacing feature 336 configured to interface with the second seal 335b, to provide contact therewith, to facilitate increased sealing of the cavity 303. It is also envisaged that the seals 335a, 335b need not necessarily be coupled to, integrally formed with or overmolded onto the housing 302, but that the seals 335a, 335b may alternatively conversely be coupled to, integrally formed with or overmolded onto the first collar 301.

In addition to or alternatively to sealing the interface between the housing 302 and the first collar 301 axially along the longitudinal direction 312, for example as in FIGS. 6 and 7, the sealing arrangement 305 may additionally or alternatively be configured to radially seal the interface between the housing 302 and the first collar 301 along a radial direction 319 that is generally normal to the longitudinal direction 312 and to the longitudinal axis 302 of the damping device 300. For example, the sealing arrangement 305 may comprise a radial seal proximate to the inner surface 320 of the cavity 303 and an axial seal proximate to the outer surface 321 of the cavity 303, or vice versa. FIGS. 8 to 11 show examples of radial sealing arrangements 305 comprising a radial seal proximate to the inner surface 320 of the cavity 303 and a radial seal proximate to the outer surface 321 of the cavity 303. These exemplary radial sealing arrangements 305, and indeed other radial sealing arrangements 305, may be employed in combination with the axial sealing arrangements 305. That is, the sealing arrangement 305 may be configured to both axially and radially seal the interface between the housing 302 and the first collar 301 simultaneously, both along the longitudinal direction 312 and along the radial direction 319.

In the example of FIG. 8, similarly to in FIG. 6, the radial sealing arrangement 305 comprises first and second O-rings 334a, 334b. The first O-ring 334a is arranged proximate to the inner surface 320 of the cavity 303, and the second O-ring 334b is arranged proximate to the outer surface 321 of the cavity 303. The example of FIG. 8 differs from that of FIG. 6 in that rather than the O-rings 334a, 334b being arranged between the housing 302 and the first collar 301 along the longitudinal direction 312, the O-rings 334a, 334b are instead arranged between the housing 302 and the first collar 301 along the radial direction 319, such that they provide for radial sealing of the interface between the housing 302 and the first collar 301 and hence of the open end 306 of the cavity 303. As described above in relation to the example of FIG. 6, it is envisaged that just one O-ring may be present, for example just the first O-ring 334a proximate to the inner surface 320, or just the second O-ring 335b proximate to the outer surface 321, or that any other number of O-rings 334a, 334b may be present, for example three or more O-rings. It is also envisaged that each of the one or more O-rings 334a, 334b need not necessarily have a circular cross-sectional profile, but may have any other suitable shape of cross-sectional profile, for example a quadrilateral or triangular shape.

In the example of FIG. 9, the radial sealing arrangement 305 comprises a first seal 335a and a second seal 335b. The first seal 335a is arranged proximate to the inner surface 320 of the cavity 303, and the second seal 335b is arranged proximate to the outer surface 321 of the cavity 303. Similarly to in the example of FIG. 7, each of the first and second seals 335a, 335b is overmolded onto the housing 302, but may otherwise be coupled to or integrally formed with the housing 302. For example, the first and second seals 335a, 335b may be overmolded onto the housing 302 from an elastomeric material, such as silicone, viton, ethylene propylene diene monomer, or nitrile rubber for example. In the example shown, each of the first and second seals 335a, 335b has a generally rectangular cross-sectional profile and is configured to protrude along the radial direction 319 towards and into the cavity 303. Each of the first and second seals 335a, 335b has a generally convex surface protruding into the cavity 303, configured to interface with the first collar 301 to provide a seal therewith. The first seal 335a may be arranged to protrude from the inner surface 320 of the cavity 303 radially outwards along the radial direction 319, and the second seal 335b may be arranged to protrude from the outer surface 321 of the cavity 303 radially inwards along the radial direction 319. In the example shown, the first and second seals 335a, 335b are substantially similar to one another in terms of the shape and size of their cross-sectional profiles, although they need not necessarily be of the same shape and size. It is also envisaged that there may be any number of one or more seals 335a, 335b, for example just a first seal 335a arranged proximate to the inner surface 320, just a second seal 335b arranged proximate to the outer surface 321, or three or more seals 335a, 335b.

FIG. 10 shows another exemplary radial sealing arrangement 305 which comprises first and second seals 335a, 335b overmolded onto the housing 302. The first seal 335a is arranged proximate to the inner surface 320 of the cavity 303, and the second seal 335b is arranged proximate to the outer surface 321 of the cavity 303. Whilst in the example shown, the first and second seals 335a, 335b are each overmolded onto the housing 302, they may otherwise be coupled to or integrally formed with the housing 302. For example, the first and second seals 335a, 335b may be overmolded onto the housing 302 from an elastomeric material, such as silicone, viton, ethylene propylene diene monomer, or nitrile rubber for example, or from a thermoplastic material, such as polyethylene, polypropylene, acrylonitrile butadiene styrene, or polycarbonate for example. As described above in relation to the example of FIG. 9, the first and second seals 335a, 335b need not necessarily have the same cross-sectional profile as each other, and there may be just one of the first or second seals 335a, 335b present, or there may be any number of one or more seals 335a, 335b present, for example three seals 335a, 335b. The seals 335a, 335b in the example of FIG. 10 differ from those in the example of FIG. 9 in that each of the seals comprises a coupling portion 326, and an inclined sealing portion 327 integrally formed with the coupling portion 326 and protruding therefrom.

In the example shown, the coupling portion 326 has a generally rectangular cross-sectional profile and is oriented to be generally parallel to the longitudinal direction 312, and the inclined sealing portion 327 is configured to protrude from the coupling portion 326 into and towards the cavity 303. Each of the inclined sealing portions 327 is configured to be angled relative to the longitudinal axis 304. The inclined sealing portion 327 of the first seal 335a is arranged to protrude radially outwards along the radial direction 319 into the cavity 303 in a longitudinal direction 312 from the proximal end 203 to the distal end 202 of the body 201. Conversely, the inclined sealing portion 327 of the second seal 335b is arranged to protrude radially inwards along the radial direction 319 into the cavity 303 in a longitudinal direction 312 from the proximal end 203 to the distal end 202 of the body 201. In the example shown, the first and second seals 335a, 335b are configured to be a mirror image of one another, in that they are substantially identical in the size and shape of their cross-sectional profiles. However, it is envisaged that the first and second seals 335a, 335b need not necessarily have the same cross-sectional profiles and that they need not necessarily be mirror images of one another. In the example shown, the inclined surface portions 327 are oriented to be angled downwards, towards the distal end 202 of the body 201, i.e. in a distal direction, to facilitate assembly of the first collar 301 into the housing 302, since the first collar 301 is configured to be fitted into the housing 302 by moving it along said distal direction, which may cause the inclined sealing portions 327 to be deformed or deflected.

In the example of FIG. 11, the radial sealing arrangement 305 similarly includes inclined features which are angled relative to the longitudinal direction 312, however these are integrally formed with, overmolded onto, or coupled to the first collar 301, rather than to the housing 302 as in the example of FIG. 10. In the example shown in FIG. 11, the first portion of the first collar 301 which is configured to be received in the cavity 303 of the housing 302 comprises two inclined protruding portions 328 which are each angled relative to the longitudinal direction 312 similarly to in the example of FIG. 10, which may be formed from a thermoplastic material, such as polyethylene, polypropylene, acrylonitrile butadiene styrene, or polycarbonate for example. One of the inclined protruding portions 328 is arranged to protrude radially inwards from an inner surface of the first collar 301 towards the inner surface 320 of the cavity 303. The other one of the inclined protruding portions 328 is arranged to protrude radially outwards from an outer surface of the first collar 301 towards the outer surface 321 of the cavity 303. The inclined protruding portions 328 are arranged to be axially aligned with one another along the longitudinal direction 312, and are shaped and sized generally to be a mirror image of one another, such that they generally form a V-shape. However, it is envisaged that the inclined protruding portions 328 need not necessarily be axially aligned with one another and that they need not necessarily have the same cross-sectional profile. It is also envisaged that there may be any number of inclined protruding portions 328, for example just one inclined protruding portion 328 arranged proximate to the inner surface 320 of the cavity 303, or just one inclined protruding portion 328 arranged proximate to the outer surface 321 of the cavity 303, or any number of one or more inclined protruding portions 328, for example three or more inclined protruding portions 328. For example, on each of an inner and/or outer surface of the first collar 301, there could be one or more inclined protruding portions 328 protruding therefrom and spaced apart from one another along the longitudinal direction 312.

Figure 12:
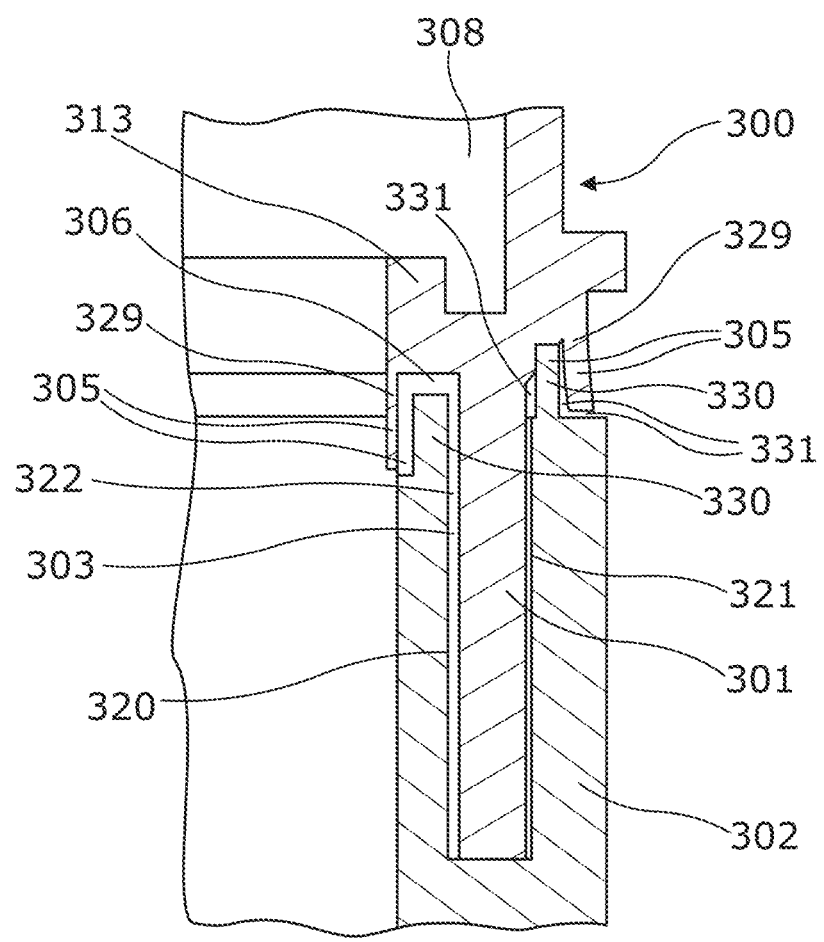
FIG. 12 shows a cross-sectional schematic view of a damping device comprising a sealing arrangement comprising a tortuous path or a labyrinth seal.

FIG. 12 shows another example of a damping device 300, in which the sealing arrangement 305 comprises a tortuous path and/or comprises a labyrinth seal, in order to impede the leakage of fluid out from the cavity 303, to seal the interface between the housing 302 and the first collar 301. In the example shown, the housing 302 and the first collar 301 are shaped such that the interface between the housing 302 and the first collar 301, for example the surfaces thereof which are arranged to be adjacent to one another, contact and/or abut one another, defines a generally tortuous fluid flow path 331. The fluid flow path 331 comprises one or more bends to make it generally tortuous or labyrinth-like. The sealing arrangement 305 comprises the fluid flow path 331 and the features of the housing 302 and/or the first collar 301 which define the tortuous path and/or the labyrinth-like arrangement. This impedes leakage of the fluid out from the cavity 303. In the example shown, the first collar 301 comprises one or more protruding portions 329 which are oriented to extend along the longitudinal direction 312 towards the housing 302. Similarly, the housing 302 comprises one or more protruding portions 330 which are oriented to extend along the longitudinal direction 312 towards the first collar 301. The protruding portions 329 are configured to fit together with the protruding portions 330 and to define the fluid flow path 331 at the interface therebetween, the fluid flow path 331 hence comprising one or more bends as a result of the geometry of the protruding portions 329, 330. In the example shown, the first collar 301 comprises two protruding portions 329, and the housing 302 comprises two protruding portions 330. However, it is envisaged that each of the first collar 301 and the housing 302 may comprise any number of one or more protruding portions 329, 330 respectively, for example they each may comprise one, two, three, four or more protruding portions 329, 330. In the example shown, each of the protruding portions 329, 330 has a generally rectangular cross-sectional profile, although it is envisaged that each of the one or more protruding portions 329, 330 may have any other suitable shape. In the example shown, each of the protruding portions 329 is integrally formed with the first collar 301, and each of the protruding portions 330 is integrally formed with the housing 302. Though, it is also envisaged that each of the protruding portions 329, 330 may be otherwise coupled to or overmolded with the first collar 301 and the housing 302 respectively, in any other suitable way.

Figure 13:
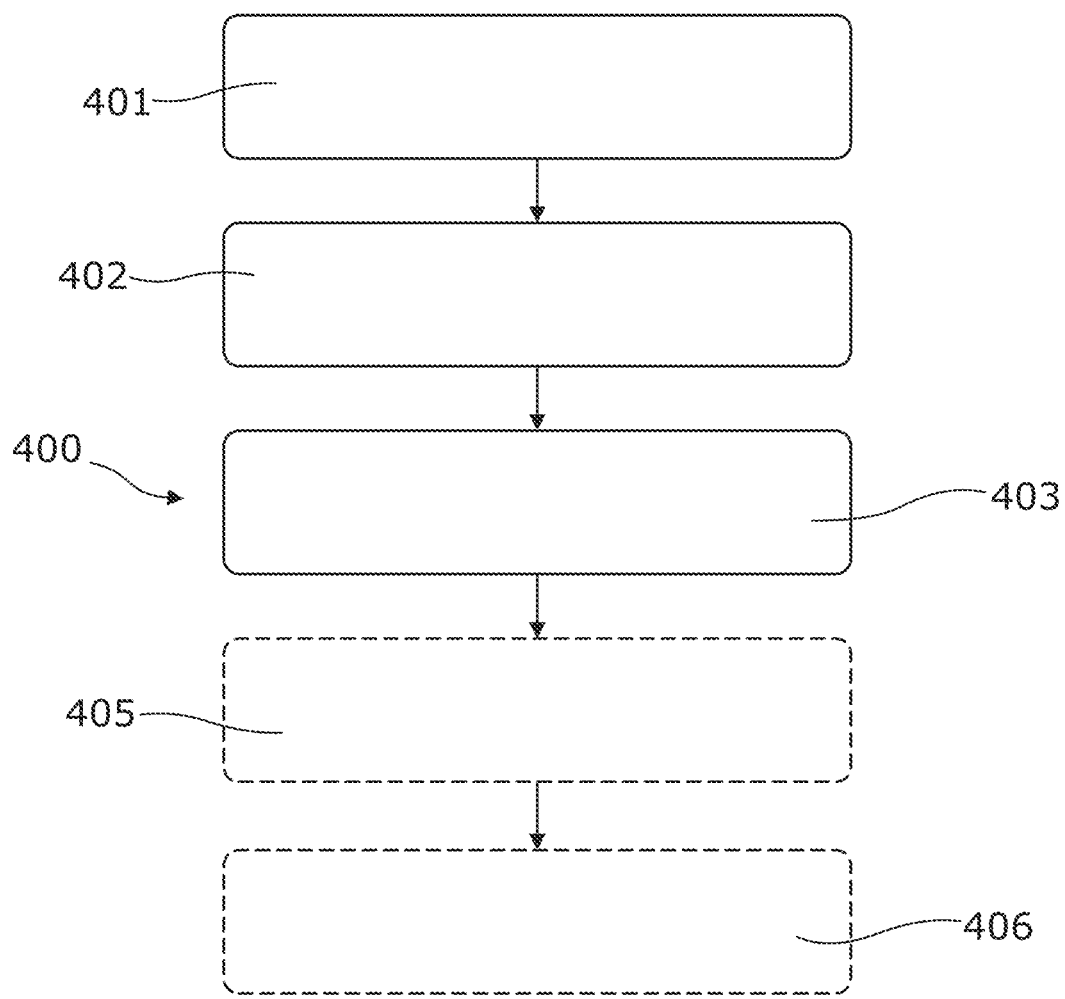
FIG. 13 shows a flowchart illustrating steps of a method of assembling a damping device.

FIG. 13 shows a flowchart illustrating a method 400 of assembling a damping device 300, for example a damping device 300 as described in the above examples. In step 401, the sealing arrangement 305 is provided. In examples wherein the sealing arrangement 305 is not coupled to or integrally formed with the housing 302 or the first collar 302, for example wherein the sealing arrangement 305 comprises a separate part or parts such as one or more O-rings 334a, 334b as in the examples of FIGS. 6 and 8, step 401 may comprise arranging the sealing arrangement 305 inside the housing 302. In examples wherein the sealing arrangement 305 is integrally formed with or coupled to the housing 302 or the first collar 301, step 401 may comprise forming the sealing arrangement 305, for example forming the housing 302 or the first collar 301, or overmolding the sealing arrangement 305 onto the housing 302 or the first collar 301. In step 402, the cavity 303 of the housing 302 is filled with fluid, for example grease. In some examples of the method 400, it is envisaged that step 402 may occur before or simultaneously with step 401. For example, where the sealing arrangement 305 comprises one or more O-rings 334a, 334b, the method 400 may comprise filling the cavity 303 of the housing 302 with fluid, and then arranging the one or more O-rings 334a, 334b in the housing 302. In step 403, the method 400 comprises arranging the first collar 301 into the cavity 303 of the housing 302, for example by moving the first collar 301 along the longitudinal direction 312 towards and into the cavity 303. Next, the method 400 may further comprise, in step 404, assembling the spring 307 with the first collar 301 to bias the first collar 301 to rotate as described above. The method 400 may also further comprise, in step 405, assembling the second collar 308 with the first collar 301.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des (B30) human insulin, Lys(B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N-(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, small modular immunopharmaceuticals (SMIP), binding-domain immunoglobulin fusion proteins, camelized antibodies, and immunoglobulin single variable domains. Additional examples of antigen-binding antibody fragments are known in the art.

The term "immunoglobulin single variable domain" (ISV), interchangeably used with "single variable domain", defines immunoglobulin molecules wherein the antigen binding site is present on, and formed by, a single immunoglobulin domain. As such, immunoglobulin single variable domains are capable of specifically binding to an epitope of the antigen without pairing with an additional immunoglobulin variable domain. The binding site of an immunoglobulin single variable domain is formed by a single heavy chain variable domain (VH domain or VHH domain) or a single light chain variable domain (VL domain). Hence, the antigen binding site of an immunoglobulin single variable domain is formed by no more than three CDRs.

An immunoglobulin single variable domain (ISV) can be a heavy chain ISV, such as a VH (derived from a conventional four-chain antibody), or VHH (derived from a heavy-chain antibody), including a camelized VH or humanized VHH. For example, the immunoglobulin single variable domain may be a (single) domain antibody, a "dAb" or dAb or a Nanobody® ISV (such as a VHH, including a humanized VHH or camelized VH) or a suitable fragment thereof. [Note: Nanobody® is a registered trademark of Ablynx N.V.]; other single variable domains, or any suitable fragment of any one thereof.

"VHH domains", also known as VHHs, VHH antibody fragments, and VHH antibodies, have originally been described as the antigen binding immunoglobulin variable domain of "heavy chain antibodies" (i.e., of "antibodies devoid of light chains"; Hamers-Casterman et al. 1993 (Nature 363:446-448). The term "VHH domain" has been chosen in order to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). For a further description of VHH's, reference is made to the review article by Muyldermans 2001 (Reviews in Molecular Biotechnology 74:277-302).

For the term "dAb's" and "domain antibody", reference is for example made to Ward et al. 1989 (Nature 341:544), to Holt et al. 2003 (Trends Biotechnol. 21:484); as well as to WO 2004/068820, WO 2006/030220, WO 2006/003388. It should also be noted that, although less preferred in the context of the present invention because they are not of mammalian origin, single variable domains can be derived from certain species of shark (for example, the so-called "IgNAR domains", see for example WO 2005/18629).

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014(E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014(E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

An example of a compound to be administered with the drug delivery device disclosed herein is a compound with the INN tirzepatide, as referenced in claim 1 of U.S. Pat. No. 9,474,780.

An example of a pharmaceutical composition to be administered with the drug delivery device disclosed herein is a pharmaceutical composition as referenced in U.S. Pat. No. 11,357,820.

An example of a pharmaceutical composition to be administered with the drug delivery device disclosed herein includes a 0.5 mL solution of 2.5 mg, 5 mg, 7.5 mg, 10 mg, 12.5 mg, or 15 mg of tirzepatide and the following excipients sodium chloride (4.1 mg), sodium phosphate dibasic heptahydrate (0.7 mg), and water for injection. Hydrochloric acid solution and/or sodium hydroxide solution may be added to adjust the pH.

An example starting dosage tirzepatide may be 2.5 mg injected subcutaneously once weekly. After four weeks, the tirzepatide dosage may be increased to 5 mg injected subcutaneously once weekly. The dosage may be further increased in 2.5 mg increments after at least four weeks on the current dose. In an example, the maximum dosage of tirzepatide may be 15 mg injected subcutaneously once weekly. If a dose is missed, patients may be instructed to administer tirzepatide as soon as possible within four days (96 hours) after the missed dose. If more than four days have passed, patients may skip the missed dose and administer the next dose on the regularly scheduled day. In each case, patients may then resume their regular once weekly dosing schedule. The day of weekly administration may be changed, if necessary. The time between two doses may be at least three days (72 hours).

Tirzepatide dosages may include 2.5 mg/0.5 mL, 5 mg/0.5 mL, 7.5 mg/0.5 mL, 10 mg/0.5 mL, 12.5 mg/0.5 mL, and 15 mg/0.5 mL. Tirzepatide may be stored in a refrigerator at 2° C. to 8° C. (36° F. to 46° F.). A single-dose pen or single-dose vial may be stored unrefrigerated at temperatures not to exceed 30° C. (86° F.) for up to 21 days. Tirzepatide may be stored in a carton.

Those of skill in the art will understand that modifications (additions and/or removals) of various components of the embodiments described herein may be made without departing from the full scope and spirit of the present invention, which encompass such modifications and any and all equivalents thereof.

LIST OF REFERENCE NUMBERS

10—device
11—housing
12—cap
13—needle sleeve
17—needle
20—distal region
21—proximal region
22—button
23—piston
200—medicament delivery device
201—body
202—distal end of the body
208—locking member
216—lock ring
217—needle
223—plunger
227—actuation member
228—button
229—dispensing mechanism
232—injection site
240—spring guide
242—protrusions
250—syringe
254—cap
258—stop
260—spring
262—spring
264—clip
265—proximal opening
266—needle shield
267—collar
268—collar
300—damping device
301—first collar
302—housing
303—annular cavity
304—longitudinal axis
305—sealing arrangement
306—open end of cavity
307—spring
308—second collar
309—plunger
310—spring carrier
311—spring guide
312—axial direction
313—first coupling element
314—receiving element
315—second coupling element
316—fixed end
317—free end
318—clip
319—radial direction
320—inner surface
321—outer surface
322—gap
323—recess
324—coupling portion
325—sealing portion
326—coupling portion
327—inclined sealing portion
328—inclined protruding portion
329—protruding portion
330—protruding portion
331—tortuous fluid flow path
332—body
333—receiving portion
334a—first O-ring
334b—second O-ring
335a—first seal
335b—second seal
336—interfacing feature
400—method
401—method step
402—method step
403—method step
404—method step
405—method step

The invention claimed is:

1. A damping device for a medicament delivery device, comprising:
    a generally cylindrical first collar;
    a housing comprising a generally annular cavity configured to receive at least a portion of the first collar;
    wherein the first collar is configured to be rotatable relative to the housing about a central longitudinal axis of the damping device, and wherein the cavity is configured to contain a fluid for impeding rotational movement of the first collar relative to the housing; and
    a sealing arrangement configured to fluidly seal an interface between the housing and the first collar.

2. The damping device of claim 1, wherein at least a portion of the first collar is received in the cavity, and wherein the cavity also contains fluid for impeding rotational movement of the first collar relative to the housing.

3. The damping device of claim 1, wherein the sealing arrangement is configured to fluidly seal an open end of the cavity at an inner interface between an inner surface of the first collar and an inner surface of the cavity and/or at an outer interface between an outer surface of the first collar and an outer surface of the cavity.

4. The damping device of claim 1, wherein the sealing arrangement comprises an axial seal arranged to fluidly seal the interface between the housing and the first collar along an axial direction that is generally parallel to the central longitudinal axis of the damping device.

5. The damping device of claim 4, wherein the axial seal comprises one or more O-rings.

6. The damping device of claim 4, wherein the axial seal comprises at least one first axial sealing element coupled to or integrally formed with the housing, and/or at least one second axial sealing element coupled to or integrally formed with the first collar.

7. The damping device of claim 1, wherein the sealing arrangement comprises a radial seal arranged to fluidly seal the interface between the housing and the first collar along a radial direction that is generally normal to the central longitudinal axis of the damping device.

8. The damping device of claim 7, wherein the radial seal comprises one or more O-rings.

9. The damping device of claim 7, wherein the radial seal comprises at least one first radial sealing element coupled to or integrally formed with the housing, and/or at least one second radial sealing element coupled to or integrally formed with the first collar.

10. The damping device of claim 9, wherein each of the at least one first and second radial sealing elements comprises an inclined portion that is angled relative to the central longitudinal axis of the damping device.

11. The damping device of claim 1, wherein the sealing arrangement is overmolded onto the housing and/or onto the first collar.

12. The damping device of claim 1, wherein at least one of the housing or the first collar is shaped such that the interface between the housing and the first collar defines a fluid flow path comprising one or more bends, wherein the sealing arrangement comprises said fluid flow path, which is generally tortuous or defines a labyrinth seal between the housing and the first collar, to impede leakage of fluid out from the cavity.

13. The damping device of claim 1, wherein the fluid comprises grease.

14. The damping device of claim 1, wherein the damping device further comprises a generally cylindrical second collar configured to circumscribe at least a portion of the first collar, wherein the first and second collars are arrangeable in a first state in which they are rotationally and axially fixed relative to one another, and a second state in which they are rotationally and axially moveable relative to one another.

15. The damping device of claim 14, wherein the first collar comprises a first coupling element configured to be received by the second collar to couple the first and second collars to one another in the first state, wherein the first coupling element is deformable or deflectable such that deforming or deflecting the first coupling element causes the first and second collars to be decouplable from one another, to permit the first collar to rotate relative to the second collar and/or to permit the second collar to axially move relative to the first collar.

16. The damping device of claim 15, wherein the first collar comprises a receiving element configured to receive a second coupling element of the second collar, wherein deforming or deflecting the first coupling element causes the first collar to rotate relative to the second collar, which causes the second coupling element to move out from the receiving element, which permits the second collar to move axially relative to the first collar.

17. The damping device of claim 1, wherein the first collar is biased to rotate relative to the housing by a biasing means, such as a spring; and wherein the first collar is arrangeable relative to the housing in a first rotational position and a second rotational position, wherein the first collar is biased towards the second rotational position by the biasing means; and wherein the fluid contained in the cavity is configured to impede rotational movement of the first collar from the first rotational position into the second rotational position, to slow down the speed at which the first collar rotates relative to the housing.

18. A medicament delivery device comprising:
a damping device comprising:
a generally cylindrical first collar;
a housing comprising a generally annular cavity configured to receive at least a portion of the first collar;
wherein the first collar is configured to be rotatable relative to the housing about a central longitudinal axis of the damping device, and wherein the cavity is configured to contain a fluid for impeding rotational movement of the first collar relative to the housing; and
a sealing arrangement configured to fluidly seal an interface between the housing and the first collar.

19. The medicament delivery device of claim 18, further comprising:
a body having a proximal end and a distal end;
a needle for injecting a medicament into a user, wherein the needle is movable relative to the body from a pre-use position to an injecting position, wherein in the pre-use position, the distal end of the needle is arranged within the body, and in the injecting position, the distal end of the needle protrudes outside of the distal end of the body for injecting medicament into the user; and
a plunger moveable relative to the body along the central longitudinal axis towards the distal end of the body from a first position to a second position, wherein the plunger is configured such that movement of the plunger from the first position into the second position causes the needle to move from the pre-use position into the injecting position,
wherein the plunger and the first collar are configured such that when the plunger is moved from the first position to the second position, the first collar is caused to rotate relative to the housing from a first rotational position into a second rotational position,
wherein movement of the first collar from the first rotational position into the second rotational position is impeded by the fluid in the cavity, and
wherein when the first collar reaches the second rotational position, the plunger is caused to move along the central longitudinal axis towards the proximal end of the body.

20. The medicament delivery device of claim 18, further comprising a medicament.

* * * * *